(12) United States Patent
Suzuki

(10) Patent No.: US 7,103,134 B2
(45) Date of Patent: Sep. 5, 2006

(54) COMPUTED TOMOGRAPHY APPARATUS

(75) Inventor: Tatsuro Suzuki, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 125 days.

(21) Appl. No.: 10/330,049

(22) Filed: Dec. 30, 2002

(65) Prior Publication Data
US 2003/0123603 A1 Jul. 3, 2003

(51) Int. Cl.
A61B 6/03 (2006.01)

(52) U.S. Cl. .......................... 378/4; 378/901

(58) Field of Classification Search .................. 378/4, 378/15, 16, 901
See application file for complete search history.

(56) References Cited

U.S. PATENT DOCUMENTS

| | | | | |
|---|---|---|---|---|
| 5,159,551 A | * | 10/1992 | Brunnett et al. ............ | 382/131 |
| 5,231,651 A | | 7/1993 | Ozaki et al. | |
| 5,291,402 A | * | 3/1994 | Pfoh .......................... | 378/13 |
| 6,061,420 A | * | 5/2000 | Strong et al. ................... | 378/4 |
| 6,173,031 B1 | | 1/2001 | Hoffman et al. | |
| 6,198,791 B1 | * | 3/2001 | He et al. ....................... | 378/19 |
| 6,285,741 B1 | * | 9/2001 | Ackelsberg et al. ......... | 378/110 |
| 6,424,692 B1 | * | 7/2002 | Suzuki .......................... | 378/4 |
| 6,639,965 B1 | * | 10/2003 | Hsieh et al. ................... | 378/8 |
| 6,650,727 B1 | * | 11/2003 | Kuroda ......................... | 378/19 |
| 6,947,584 B1 | * | 9/2005 | Avila et al. .................. | 382/131 |
| 2003/0076919 A1 | * | 4/2003 | Suzuki .......................... | 378/4 |
| 2003/0076920 A1 | * | 4/2003 | Shinno et al. ................. | 378/4 |
| 2004/0131139 A1 | * | 7/2004 | Oota et al. ..................... | 378/4 |

* cited by examiner

Primary Examiner—Edward J. Glick
Assistant Examiner—Krysytna Suchecki
(74) Attorney, Agent, or Firm—Oblon, Spivak, McClelland, Maier & Neustadt, P.C.

(57) ABSTRACT

A computed tomography apparatus configured to assist an operator in easily and correctly making an imaging plan thereby reducing the burden of the operator. The computed tomography apparatus selects at least one of reconstruction methods or changes a parameter by the information the operator inputs or displays its grade information, for example.

15 Claims, 19 Drawing Sheets

| RECONSTR-UCTION METHOD | X-RAY DOSE | | SCANNING TIME | TOTAL TIME | QUALITY OF IMAGE | X-RAY TUBE OLP |
|---|---|---|---|---|---|---|
| | WIDE RANGE | NARROW RANGE | | | | |
| FAN-BEAM RECONSTR-UCTION METHOD | E | B | B | E | B | B |
| CONE-BEAM RECONSTR-UCTION METHOD | B | E | E | B | E | E |

GRADE INFORMATION

PROCESS AFTER DATA COLLECTION
XXXXXXXXX
XXXXXXXX

PATIENT INFORMATION
XXXXXXXXXX
XXXXXXXXXX

[B1] [B2] [B3] [B4] [B5] [C]

-105.5
-405.5

SN

| No. | START TIME | PAUSE TIME | START POSITION | STOP POSITION | SCAN MODE | HELICAL PITCH | MAIN SCAN NUMBER | CONTINU-ATION SCAN KV | CONTINU-ATION SCAN mA | CONTINU-ATION SCAN SPEED | CONTINU-ATION SCAN FOV | RECONSTRUCTION PARAMETER IMAGE SLICE WIDTH | RECONSTRUCTION PARAMETER RANGE | WINDOW CONDITIONS | AMOUNT OF MOVEMENT |
|---|---|---|---|---|---|---|---|---|---|---|---|---|---|---|---|
| 1 | 30.0 | 30.0 | -105.5 | -405.5 | Helical | 3.5 | 1 | 120 | 300 | 0.5 | 320 (M) | 3mm X 4 | 300.0 | OUT | 300.0 |
| 2 | 1:00.0 | 6.0 | -105.5 | -405.5 | Helical | 3.5 | 1 | 120 | 300 | 0.5 | 320 (M) | 3mm X 4 | 300.0 | OUT | 300.0 |
|   |   |   |   |   |   |   |   |   |   |   |   |   |   |   |   |
|   |   |   |   |   |   |   |   |   |   |   |   |   |   |   |   |
|   |   |   |   |   |   |   |   |   |   |   |   |   |   |   |   |

4 SEGMENTS COLLECTION
HELICAL PITCH 3.5

FIG. 15

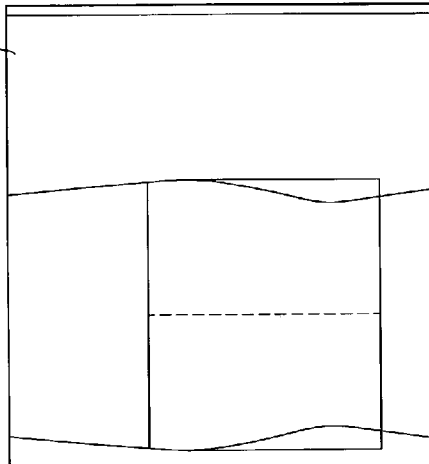

PROCESS AFTER DATA COLLECTION
XXXXXXXXX
XXXXXXXXXX

PATIENT INFORMATION
XXXXXXXXXX
XXXXXXXXXX

B1　B2　B3　B4　B5　C

| | | | | | | | MAIN | CONTINU-ATION SCAN | | RECONSTRUCTION PARAMETER | EXTEN-TION | WINDOW CONDITIONS |
|---|---|---|---|---|---|---|---|---|---|---|---|---|
| No. | START TIME | PAUSE TIME | START POSITION | STOP POSITION | SCAN MODE | HELICAL PITCH | RECONSTRUCTION METHOD | RECONSTRUCTION THICKNESS (mm) | IMAGE PITCH (mm) | RECONSTRUC-TION SIZE | MATRIX SIZE | THRESHOLD VALUE |
| 1 | 30.0 | 30.0 | -105.5 | -405.5 | Helical | 7 | CORN | 1 | 1 | XXXXX | XXXX | XXX |
| 2 | 1:00.0 | 6.0 | -105.5 | -405.5 | Helical | 7 | CORN | 1 | 1 | XXXXX | XXXX | XXX |

RECONSTRUCTIN THICKNESS 0.5mm, IMANG PITCH 0.5mm

FIG. 19

| HELICAL PITCH | MAIN NUMBER OF SCAN | KV | mA | IMAGE SLICE WIDTH |
|---|---|---|---|---|
| 7 | 1 | 120 | 130 | 3mm X 4 |

FIG. 21

| RECONSTRUCTION PARAMETER | |
|---|---|
| RECONSTRUCTION THICKNESS | RECONSTRUCTION PITCH (mm) |
| 0.5 | 1 |

COMPUTED TOMOGRAPHY APPARATUS

CROSS-REFERENCE TO RELATED APPLICATIONS

This application claims priority under 35 U.S.C. § 119 to Japanese patent application No. P2001-399359 filed Dec. 28, 2001 and Japanese patent application No. P2002-353873 filed Dec. 5, 2002, the entire contents of which are incorporated by reference herein.

BACKGROUND OF THE INVENTION

The present invention relates to a computed tomography apparatus which takes an image of an object and can reduce the burden of an operator who makes an imaging plan.

An example of a computed tomography apparatus is an X-ray computed-tomography apparatus (hereafter called X-ray CT apparatus). A specific implementation of an X-ray CT apparatus, a multi-slice X-ray CT apparatus has been developed and has found widespread use in recent years. A multi-slice X-ray CT apparatus has a 2-dimensional detector including M channels of N segments detection elements where a plurality of channel detection elements are arranged along the segment direction perpendicular to the channel direction. A multi-slice X-ray CT apparatus collects an image which is characterized by having high resolution and wide range. Examples of multi-slice X-ray CT apparatus include 4 slice type, 8 slice type, and 16 slice type devices . . .

An example of a reconstructing method used with the multi-slice X-ray CT apparatus is a fan-beam reconstruction method which reconstructs the image on the assumption an X-ray beam is parallel to a direction perpendicular to a slice direction although the X-ray beam is, to be exact, a cone-like X-ray beam (cone-beam) which spreads in the slice direction. Another example of a reconstructing method is a cone-beam reconstruction method which reconstructs the image on basis of the angle of the cone-beam. The cone-beam reconstruction method is used when the number of slices to be simultaneously detected equal 8 and the fan-beam reconstruction method is used when the number of slices equal 4.

There are merits and demerits in these reconstruction methods, respectively. For example, the cone-beam reconstruction method makes excellent quality images but requires a longer reconstruction time as compared with the fan-beam reconstruction method because of the need to account for the cone angle. Thus, it is necessary for an operator to understand the special features of each of these reconstruction methods when choosing an appropriate reconstruction method for each patient and for specific images of patients. Setting up the equipment between shots with different methods is very difficult for an operator. Even if the operator is well-skilled in setting up the equipment, this set-up process takes much time and the patient processing efficiency (patient throughput) decreases. Although conventional imaging plan systems configured to assist the operator are known, they do not urge the operator to determine the reconstruction method according to scanning conditions.

In addition, there is another factor which causes a decrease in patient throughput. Another example of a multi-slice X-ray CT apparatus is a multi-slice (e.g., 4 slice or 8 slice) helical X-ray CT apparatus which performs a helical scan. With a multi-slice helical apparatus, the operator can choose the image slice width, thereby creating an imaging plan. The image slice width is defined as the number of imaging slices times the thickness of an imaging slice. The image slice width is also called a scan slice. The thickness of the imaging slice is defined by the thickness of the slice in a rotation center position and desired value is selected (e.g., from 0.5 mm, 1 mm, 2 mm, 3 mm and 4 mm). Thus, the number of imaging slices is the number of detection element segments corresponding to the thickness of the imaging slice (e.g., 0.5 mm).

There are a number of limitations associated with a conventional multi-slice helical X-ray CT apparatus. For example, after the operator sets that the number of imaging slices (e.g., =8) and a helical pitch (e.g., =7), before imaging, the operator may change the number of imaging slices (e.g., from 8 to 4) in response to various demands (quality of image, imaging speed, etc.) changes. It is possible in this case for an object to be imaged with the number of slices=4 and the helical pitch remaining equal to 7 if the operator forgets to change the helical pitch. As a result, an artifact will appear on the reconstructed image. (Note helical pitch is defined as the distance of the movement of the X-ray beam along the rotation axis when it makes a turn around the patient divided by the thickness of the imaging slice.) If the image many such artifacts, it is necessary to re-image the patient and patient throughput decreases.

SUMMARY OF THE INVENTION

It is an object of the present invention to supply a computed tomography apparatus which assists the operator in easily and correctly making an imaging plan.

One embodiment of the present invention includes a computed tomography apparatus comprising a radiation source configured to emit a radiation to an object, a detector configured to detect the radiation from the object, a data collection unit configured to collect projection data based on an output signal of the detector, an input device configured to input an image slice width of the object and a controller configured to select at least one of reconstruction methods which can be used according to the inputted image slice width and to control a display so as to display the selected reconstruction method on a display.

A further embodiment of the present invention includes a computed tomography apparatus comprising a radiation source configured to emit a radiation to an object, a detector configured to detect the radiation from the object, a data collection unit configured to collect projection data based on an output signal of the detector and a controller configured to control a display so as to display at least one of reconstruction methods and its grade information on a display.

A further embodiment of the present invention includes a computed tomography apparatus comprising a radiation source configured to emit a radiation to an object, a detector configured to detect the radiation from the object, a data collection unit configured to collect projection data based on an output signal of the detector, an input device configured to input an image slice width of the object, a controller configured to perform a priority processing or an examination processing about typical feature of each reconstruction method; and a reconstruction unit configured to reconstruct an image of the object on the basis of the projection data by the reconstruction method determined according to the image slice width and a result of a priority processing or an examination processing.

A further embodiment of the present invention includes a computed tomography apparatus comprising a radiation source configured to emit a radiation to an object, a detector configured to detect the radiation from the object, a data collection unit configured to collect projection data based on an output signal of the detector, an input device configured to input the information related to an imaging range of the object, a controller configured to select one reconstruction method according to the inputted information and a reconstruction unit configured to reconstruct an image of the object on the basis of the projection data by the selected reconstruction method.

A further embodiment of the present invention includes a computed tomography apparatus comprising a radiation source configured to emit a radiation to an object, a detector configured to detect the radiation from the object, a data collection unit configured to collect projection data based on an output signal of the detector, a memory unit configured to store a plurality of reconstruction methods, an input device configured to input the information related to an imaging range of the object, a controller configured to select at least one of reconstruction methods from the reconstruction methods stored in the memory unit according to the inputted information and to display the selected reconstruction method on a display, a select device where an operator selects one reconstruction method from at least one of reconstruction methods displayed on the display and a reconstruction unit configured to reconstruct an image of the object on the basis of the projection data by the selected reconstruction method.

A further embodiment of the present invention includes a computed tomography apparatus comprising a radiation source configured to emit a radiation to an object, a detector including a plurality of detection elements configured to detect the radiation from the object, a data collection unit configured to collect projection data based on an output signal of the detector, a mechanism configured to move the detector to the object helically by a helical pitch, an input device configured to change the number of image slices of the object and a controller configured to change the helical pitch according to the number of image slices.

A further embodiment of the present invention includes a computed tomography apparatus comprising a radiation source configured to emit a radiation to an object, a detector including a plurality of detection elements configured to detect the radiation from the object, a data collection unit configured to collect projection data based on an output signal of the detector, an input device configured to change the number of image slices of the object and a controller configured to change a current of the radiation source according to the number of image slices.

A further embodiment of the present invention includes a computed tomography apparatus comprising a radiation source configured to emit a radiation to an object, a detector including a plurality of detection elements configured to detect the radiation from the object, a data collection unit configured to collect projection data based on an output signal of the detector, a mechanism configured to move the detector to the object helically by a helical pitch, an input device configured to change the number of image slices of the object and a controller configured to give an alarm in order to urge an operator to confirm the helical pitch when the number of image slices is changed.

A further embodiment of the present invention includes a computed tomography apparatus comprising a radiation source configured to emit a radiation to an object, a detector including a plurality of detection elements configured to detect the radiation from the object, a data collection unit configured to collect projection data based on an output signal of the detector, an input device configured to change reconstruction thickness of an image of the object, a controller configured to change image pitch according to the changed reconstruction thickness and a reconstruction unit configured to reconstruct the image of the object on the basis of the projection data by the changed image pitch.

A further embodiment of the present invention includes a computed tomography apparatus comprising a radiation source configured to emit a radiation to an object, a detector including a plurality of detection elements configured to detect the radiation from the object, a data collection unit configured to collect projection data based on an output signal of the detector, an input device configured to change reconstruction thickness of an image of the object and a controller configured to give an alarm in order to urge an operator to confirm the image pitch when the reconstruction thickness is changed.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 8A and 8B is an illustration of an example displayed on a monitor in the second creation mode;

FIG. 13 is an illustration of an example displayed on a monitor in the second embodiment;

FIG. 15 is an illustration of an example displayed on a monitor in the first modification of the second embodiment;

FIG. 19 is an illustration of an example displayed on a monitor in the second modification of the second embodiment;

FIG. 21 is an illustration of an example displayed on a monitor in the third modification of the second embodiment.

DETAILED DESCRIPTION OF THE INVENTION

Figure 1:
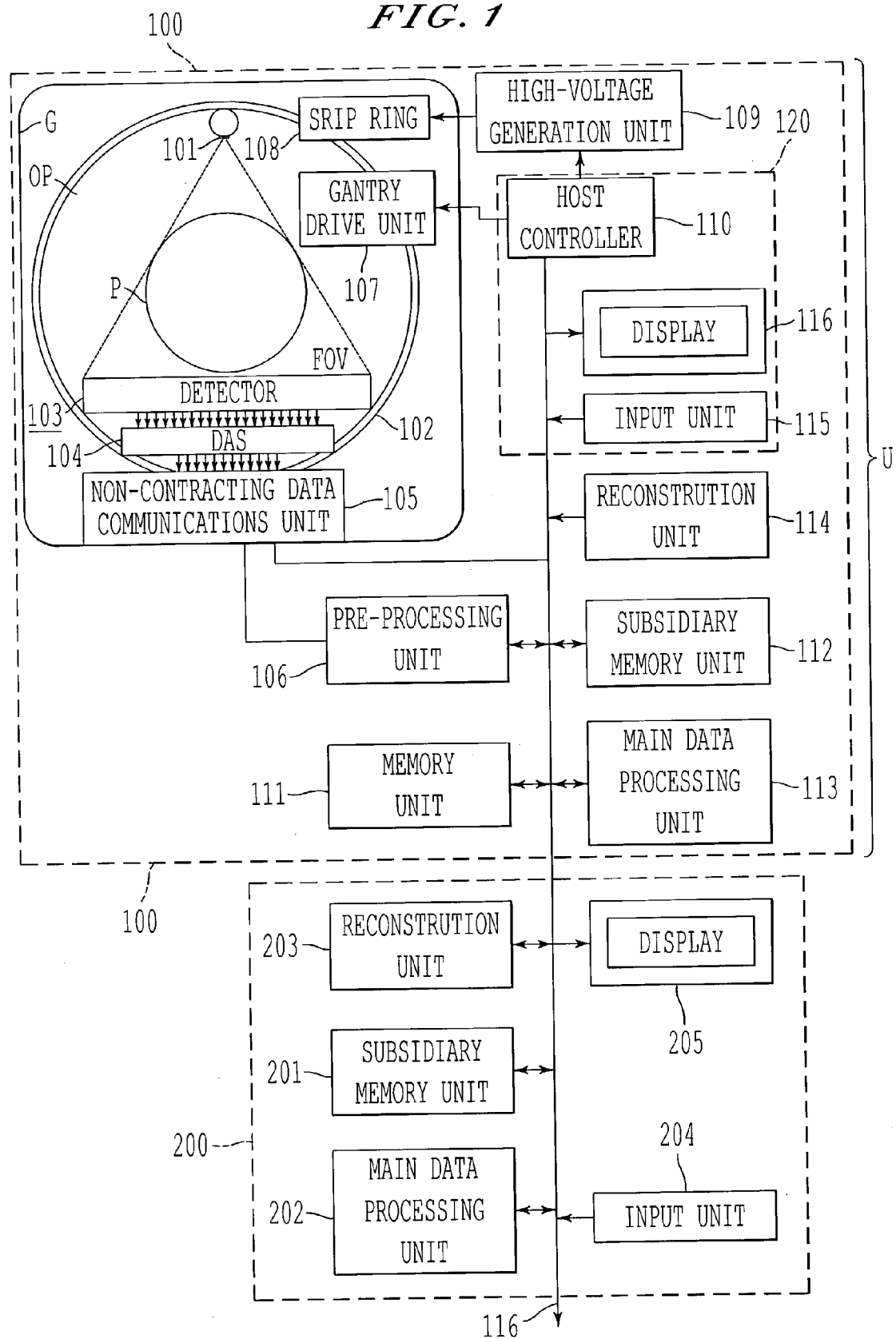
FIG. 1 is a block diagram showing an X-ray CT apparatus according to the first embodiment of the present invention.

The first embodiment which is one example according to the present invention will be explained reference to FIGS. 1 to 10. The first embodiment is an example which selects automatically a reconstruction method which can be used and displays it on the basis of the information inputted by the operator. FIG. 1 is a block diagram showing a multi-slice X-ray CT apparatus which is one example of a computed tomography apparatus according to the first embodiment. The multi-slice CT apparatus can perform not only a multi-slice helical scan but also a conventional scan (single slice scan or multi-slice scan).

The X-ray CT apparatus 100 has a bed where an object, such as a patient, is laid, a gantry G which has an opening space OP and collects projection data of the patient in it, and a data processing unit U which controls the whole of the gantry G and reconstructs an image from the projection data and displays it on a monitor. The bed has a plate which can be slid in the longitudinal direction by a bed control unit. Usually, the patient is laid so that the body axis direction is along the longitudinal direction.

The gantry G has an X-ray tube 101, as one example of a radiation source, and an X-ray detector 103, as one example of a radiation detector, arranged opposite the X-ray tube 101 such that the patient P inserted in the opening space OP is positioned between them. Furthermore, the gantry G includes a switch group 103a (refer to FIG. 3), the data acquisition system (DAS) 104, a non-contacting data communications unit 105, a gantry drive unit 107, and a slip ring 108. The X-ray tube 101, the X-ray detector 103, and the data acquisition system 104 are fixed in a rotation ring 102 which can rotate within the gantry G. The rotation ring 102 rotates with the X-ray tube 101, the X-ray detector 103, and the data acquisition system 104 around a rotation center axis parallel to the body axis of the patient P inserted into the opening space OP of a gantry G by a gantry drive unit 107. The rotation ring 102 rotates at high-speed speed, such as less than one second per rotation.

The X-ray tube 101 generates cone-beam (four-sided pyramid-like) X-rays to the patient P laid in the field of view (FOV). An electrical power (tube voltage, tube current) required for emitting of the X-ray is supplied to the X-ray tube 101 through the slip ring 108 from a high-voltage generating unit 109. Thereby, the X-ray tube 101 generates the cone-beam which spreads in two directions of a slice direction parallel to the above-mentioned rotation center axis and a channel direction perpendicular to the slice direction. In addition, between the X-ray tube 101 in gantry G and the patient P, there is a collimator which forms the appropriate size X-ray beam emitted from focus of the X-ray tube 101. The X-ray detector 103 is a device which detects the X-ray which penetrated patient P and includes X-ray detection elements arranged in the shape of an array in the two directions (the slice direction and the channel direction). In the first embodiment, the X-ray detector 103 has a plurality of detector modules (for example, 38 pieces) arranged in the channel direction.

Figure 2:
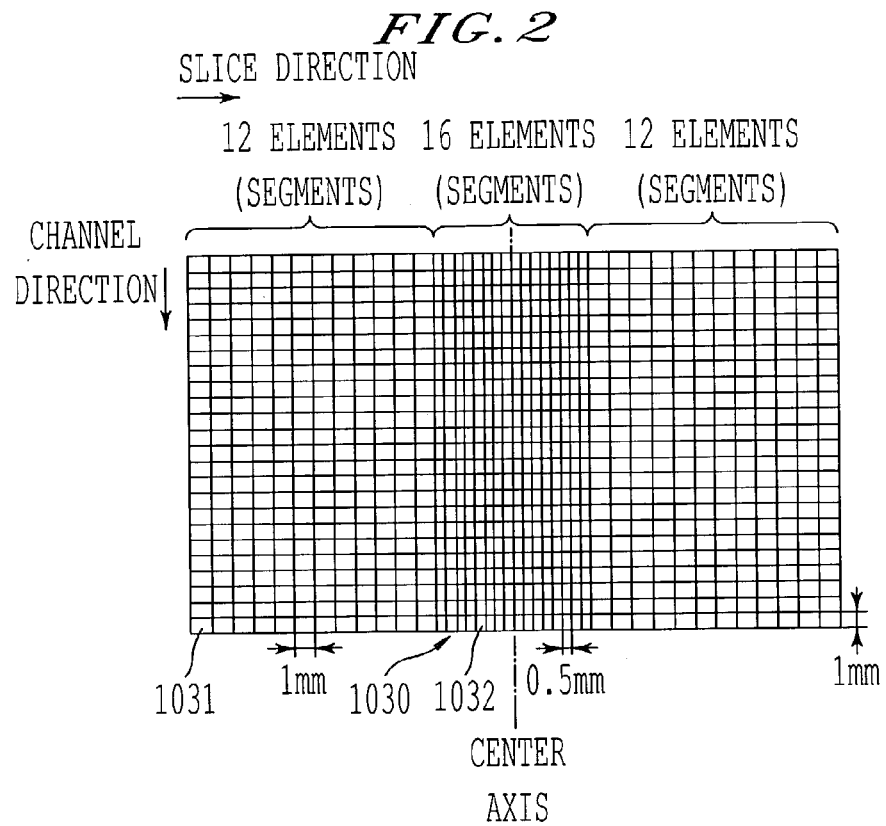
FIG. 2 is a plane view showing a detector module which an X-ray detector includes.
Figure 3:
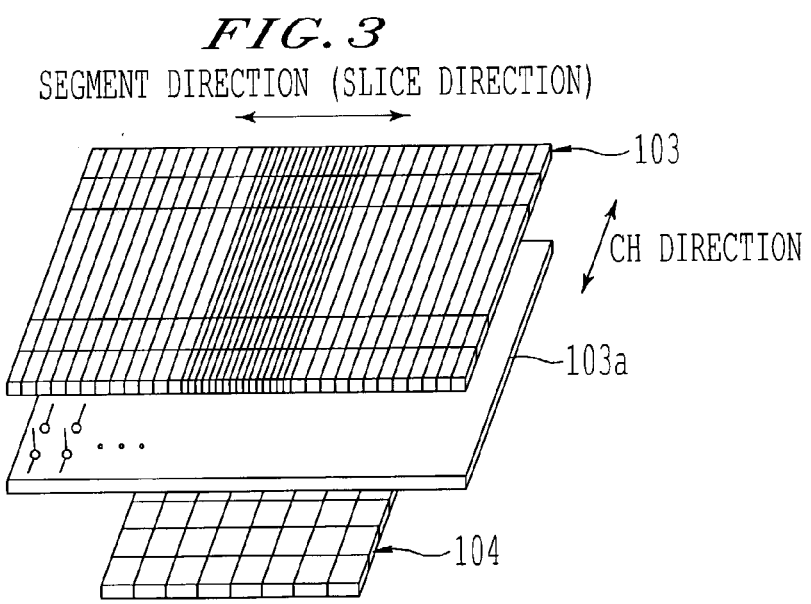
FIG. 3 is a perspective view showing an X-ray detector, a switch group and a data acquisition system (DAS)

FIG. 2 is a plane view showing one detector module 1030. FIG. 3 is a perspective view showing the 2-dimensional X-ray detector 103, the switch group 103a and the DAS 104. The detector module 1030 has a scintillator and a photo-diode tip which has a plurality of detection elements 1031 and 1032 each of which includes a photo-diode. The detection elements 1031 and 1032 are arranged in the shape of a matrix in the two directions of the channel direction and the slice direction. In addition, with the X-ray CT apparatus in the first embodiment, the detector modules 1030 are arranged in the array shape centering on the focus of the X-ray tube 101 rather than in a flat shape. The detector module 1030 has the above-mentioned photo-diode tips, switching tips included in the switch group 103a, and a DAS tip included in the DAS 104. The switch group 103a mounts switching elements, such as FET, for example, on a switch board. The photo-diode tips, the switching tips, and the DAS tips are mounted on a single rigid printed wired board.

Moreover the detection element 1031 has the sensitivity area where the X-ray can be detected. The width of the sensitivity area of the detection element 1031 is 1.0 mm in the slice direction and 0.5 mm in the channel direction. While, the width of the sensitivity area of the detection element 1032 is 0.5 mm in the slice direction and 0.5 mm in the channel direction. The width of the sensitivity area is defined as the width on the rotation center axis. That is to say, "the photo-diode has 1 mm sensitivity area" means "the photo-diode has the sensitivity are which is equivalent to 1 mm on the rotation center axis of the X-ray tube." As the X-ray spreads in the shape of radiation, the width of actual sensitivity on the photo-diode is larger a little than 1 mm according to both of the distance between the X-ray focus and the rotation center axis and the distance between the X-ray focus and the photo-diode. As shown in FIG. 2, sixteen detection elements 1032 of 0.5 mm width are put in the slice direction, for example. A group of the sixteen detection elements 1032 is called hereinafter the first detection elements segment. Moreover, on both sides of the first detection elements segment in the slice direction, there are twelve detection elements 1031, for example, of 1 mm width than the number of the detection elements 1032. Each group of the twelve detection elements 1031 put in the slice direction is called hereinafter the second detection elements segment. In the first embodiment, the X-ray detector is designed such that the number (for example, 16 elements) of the detection elements 1032 put in the slice direction is more than each number (for example, 12 elements) of the detection elements 1031 arranged at each side, and is less than the total number (for example, 24 elements) of the detection elements 1031. That is, in the first embodiment, there are 912 detection elements in the channel direction (line direction) and 40 detection elements in the slice direction (segment direction). In addition, although the X-ray detector 103 in the first embodiment has the 2-dimensional detector including unequal width detection elements that are the 0.5 mm detection elements and the 1.0 mm detection elements, a 2-dimensional detector which has equal width detection elements may be used. Furthermore, the size of the detection element is not limited to the first embodiment, such as 0.5 mm and not 1.0 mm but 1.25 mm width, for example.

The DAS 104 which has data collection elements, such as 912 lines times 8 segments or 912 lines times 4 segments. The number of the data collection elements is fewer than that of the detection elements, such as 912 lines times 40 segments. The detected data is sent to the switch group 103a which adds the data in the slice direction in the control of a host controller 110, and transmitted to the DAS 104. The projection data outputted from the DAS 104 is transmitted to the below-mentioned a data processing unit U through the non-contacting data communications unit 105 which uses an optical communication device. The slip ring may be used for the data communication instead of the optical communication device. The data collection repeats at high speed, such as about 1000 times per a rotation.

In the DAS 104, it is determined according to the reconstruction method, the fan-beam reconstruction method or the cone-beam reconstruction method, in a imaging plan as described below, whether eight data collection elements or four data collection elements. That is to say, the number of data collection elements used depends on the reconstruction method. In the first embodiment, when performing the fan-beam reconstruction method (for example, 2 mm and 4 slices etc.), four data collection elements (for example, 912 lines and 4 segments) are used, while, when performing the cone-beam reconstruction method (for example, 0.5 mm and 8 slices etc.), eight data collection elements (for example, 912 lines and 8 segments) are used.

The data processing unit U has mainly the host controller 110, a pre-processing unit 106 which pre-processes the projection data, such as data compensation, a memory unit 111, a subsidiary memory unit 112, a main data processing unit 113, a reconstruction unit 114, an input unit 115, and a display 116 which are mutually connected through a data control bus 116. Furthermore, the data control bus 116 is connected to an external image processing unit 200. The image processing unit 200 includes a subsidiary memory unit 201, a main data processing unit 202, a reconstruction unit 203, an input unit 204, and a display 205.

The pre-processing unit 106 performs the sensitivity compensation or X-ray strength compensation, etc. of the projection data transmitted from the non-contacting data communications unit 105. 360 degrees, 1000 sets of the 2-dimensional projection data performed the sensitivity compensation or the X-ray strength compensation with the pre-processing unit 106 are once stored in the memory unit 111. Moreover, an imaging planning program which is a program for carrying out the above-mentioned imaging plan is stored in the subsidiary memory unit 112. The reconstruction unit 114 reconstructs slice image data on the basis of the projection data stored in the memory unit 111 by the fan-beam reconstruction method or the cone-beam reconstruction method. The cone-beam reconstruction method uses algorithm called Feldkamp method. The Feldkamp method is approximate reconstruction method improved on the basis of the fan-beam convolution back projection method in order to treat the wide range in the slice direction as a group of a plurality of box data cells and to make the 3-dimensional distribution data (hereinafter called volume data which a plurality of data cells are gathered 3-dimensionally)) of an X-ray absorption coefficient. That is, in the Feldkamp reconstruction method, the projection data is convoluted as the fan projection data, and the convoluted data is back-projected along with a slant ray according to the actual cone angle to the rotation center axis.

Furthermore, if one or more of the following compensation processes are performed in reconstruction process by the cone-beam reconstruction method, the error of reconstruction can be reduced. The first compensation process compensates the error caused by the reason that the X-ray beam passes long inside of the patient long since the X-ray beam is aslant. That is, it compensates the projection data (the pre-processing may not be performed) for the difference length according to the position in the slice direction.

The second compensation process compensates the error caused by the reason that the actual X-ray path is different from the calculated path between the X-ray focus and the center of the box data cell in the reconstruction process.

That is, the projection data detected along with a plurality of the actual X-ray paths near the calculated paths is changed to the back-projection data along with the calculated path. The back-projection data is weighted and back-projected. Especially in the helical scan, since the position between the X-ray focus and the reconstructed slice changes in the slice direction, it is desirable to change the weight of the data according to the position. In the above-mentioned cone-beam reconstruction method, a large detector in the slice direction is effectively used. In addition, another algorithm of this cone-beam reconstruction method using the cone angle information like ASSR method described in Japanese patent publication No. 8-187240 may be used, for example. The ASSR method is that the approximation projection data on the X-ray path approximated to the position of the virtual plane (being set up as a slanting plane which inclines to the center axis of the helical scan is more effective) obtained from 2-dimensional projection data is extracted.

While, the fan-beam reconstruction method uses the fan-beam back projection method, as described in Japanese patent publication No. 10-248837, where the image is reconstructed as the X-ray is perpendicular to the rotation center axis (the projection data is assumed to be obtained by the X-ray perpendicular to the body axis direction). In the fan-beam reconstruction method, the main data processing unit 113 performs a helical compensation to the projection data. In the helical compensation, projection data (360 degrees projection data or 180 degrees+fan angle data) is obtained by a line-compensation of the same phase projection data near the slice. In the first embodiment, the helical compensation is improved. The main data collection unit 113 pre-sets re-sampling points of a predetermined number in the predetermined range near the slice, obtains the re-sampling data by inter-compensating at the re-sampling points, and makes the projection data of the slice by weighting the re-sampling data with a filter. The reconstruction unit 114 generates the image from the projection data by the fan-beam reconstruction method. While, in the cone-beam reconstruction method, the above-mentioned first and second compensations are used instead of the helical compensation.

The reconstructed volume data is directly or once stored in the memory unit 111, transmitted to the data processing unit 113. The volume data is changed to the image, such as a slice image, a sectional image and a so-called 3-dimensional image data which is a 3-dimensional surface image of the specific organs by rendering processing. The image is displayed on the display 116.

The operator can select the image among the above-mentioned images according to the purpose of inspection and diagnosis. In this case, the image is generated and displayed in a different form from the same volume data. Moreover, the operator can select the first mode where one image selected is displayed or the second mode where a plurality of the images are displayed simultaneously according to the purpose.

The host controller 110 controls each unit as described below and collects the X-ray penetration data (projection data). Namely, the host controller 110 stores in an internal memory the scanning conditions, such as slice thick, inputted through the input unit 115 by the operator. On the basis of the stored or inputted directly scanning conditions, the high-voltage generating unit 109, a bed drive unit, and the gantry drive unit 107 are controlled. In detail, the amount of sliding of the bed to the body axis direction, the sliding speed, the rotation speed of the gantry (the X-ray tube 2014 and the detector 103), a rotation pitch and the timing of the X-ray, etc. are controlled. Thereby, the cone X-ray beam is emitted to the field of view of the patient from many directions, the penetrated X-ray is detected by each detection element of the detector 103. The host controller 110 controls ON/OFF of the switching elements of the switch group 103a according to the scanning conditions (especially image slice width (the number of imaging slices times the thickness of the imaging slice)) set up with the input unit 115. Thereby, addition of the signals between the segments is performed before DAS by which the connection between the detection elements (photo-diodes) of the X-ray detector 103 and the data collection elements of the DAS 104 is changed according to the thickness of the imaging slice. In addition, according to the thickness of the imaging slice, the collection data of DAS 104 can also be added by processing, which is called addition after DAS. The processing of the addition can be performed with the pre-processing unit 106.

Moreover, in addition to control of the connection state of switch group 103a mentioned above, the host controller 110 switches the number (for example, four segments for the fan-beam reconstruction method or eight segments for the cone-beam reconstruction method) of the DAS segments in the slice direction used for the data collection. The X-ray projection data of a plurality of slices corresponding to the scanning conditions or the reconstruction conditions is outputted from the DAS 104. Among the data processing unit U mentioned above, the host controller 110, the input apparatus 115 and the display 116 are an interactive interface between the apparatus and the operator. The interactive interface is used as an imaging planning creation system 120 when the operator makes the imaging plan before actual scan according to the imaging planning program stored in the subsidiary memory unit 112.

The imaging planning creation function of the imaging planning creation system 120 includes the input and set of many conditions, such as FOV, the flow from the scan to the record, the scanning conditions, the reconstruction conditions, and the image display/record conditions.

Generally, the set of the scanning conditions, such as tube voltage, tube current, and the timing of the X-ray, and the reconstruction conditions, such as the image slice width (the thickness of the imaging slice times the number of slices) and matrix size, needs special knowledge. Since the function is based on the special knowledge, even a novice operator can make an equivalent imaging plan.

As the flow from the scan to the record, there is a flow of conventional scan which repeats the bed movement after the scan during the bed stop. Additionally, with the conventional scan, there are scan-scan mode which reconstructs and displays images after the scan of the total slices is completed and scan-view mode which repeats the scan by the reconstruction/display of the image in each position.

While, as the flow of the helical scan, there are auto filming mode which performs the fan-beam reconstruction or the cone-beam reconstruction following the helical scan and makes films according to the predetermined window conditions while displaying images on the display, active auto filming mode which enables the operator to adjust the window conditions, if necessary, during the scan and suspends filming during adjustment of the window conditions, and real time mode which performs a real time reconstruction following the helical scan and makes films of the image obtained by the fan-beam reconstruction or the cone-beam reconstruction which different from the real time scan.

The helical scan (called corkscrew scan or spiral scan) moves the patient, rotating the source of the X-ray continuously in the case of the third generation or the forth generation type of the X-ray CT apparatus. In this helical scan, the position of the patient changes continuously during emission of the X-ray according to the rotation angle of the source of the X-ray. That is, the position of the scanning plane to the patient changes continuously.

A plurality of parameters are concerned with collection operation (scanning operation) of the projection data. A plurality of parameters are concerned also with reconstruction operation which reconstructs images on the basis of the collection signals and image display operation which displays images, respectively.

As the scanning conditions (signal collection parameters), there are an imaging part of the patient (a whole body, a head, a chest, a lung, a leg, etc.), a scan type (conventional scan (multi-slice scan or single slice scan) and helical scan), the thickness of the imaging slice, a slice interval, the number of the slices used for the multi-slice scan, volume size, the tilt angle of the gantry, tube voltage, tube current, the size of FOV, scanning speed (rotation speed of the X-ray tube and the detector) and the distance of the bed movement while the X-ray tube and the X-ray detector rotates around the patient once, for example. While, as the reconstruction conditions, there are the reconstruction method (the fan-beam reconstruction method or the cone-beam reconstruction method), a reconstruction thickness of the image, the pitch between images (image generation pitch), reconstruction size, reconstruction matrix size, and a threshold which extracts an interested part, for example. Furthermore, as image display/record conditions (image display/record parameter), there are a window level, window width, display magnification, and multi-planer (sagittal, coronal, oblique, etc).

In this first embodiment, when the operator sets the reconstruction method (the fan-beam reconstruction method or the cone-beam reconstruction method), effective reference information for the setting of the reconstruction method can be displayed, or the reconstruction method can be automatically selected according to the required information inputted by the operator since the operator can communicate the apparatus interactively with the input unit 115. For this, the first to third creation modes are prepared as shown in FIGS. 5 to 10.

In order to complete the imaging sequence from the signal collection to the image display through the image reconstruction, it is required that the scanning conditions mentioned above, reconstruction conditions, and image display/record conditions are set up, respectively. The flow to set these conditions (parameters), such as the signal collection, the reconstruction, the image display/record is called a plan. The operator makes the plan where the scanning conditions, the reconstruction conditions, and the image display/record conditions can be included in order to make it convenient. By choosing the plan, a series of above-mentioned whole conditions can be set easily. Under support of the imaging planning creation system 120, the operator sets up the imaging plan (schedule). According to the set-up schedule, the host controller 110 controls the gantry and the bed to perform the schedule one by one.

Figure 4:
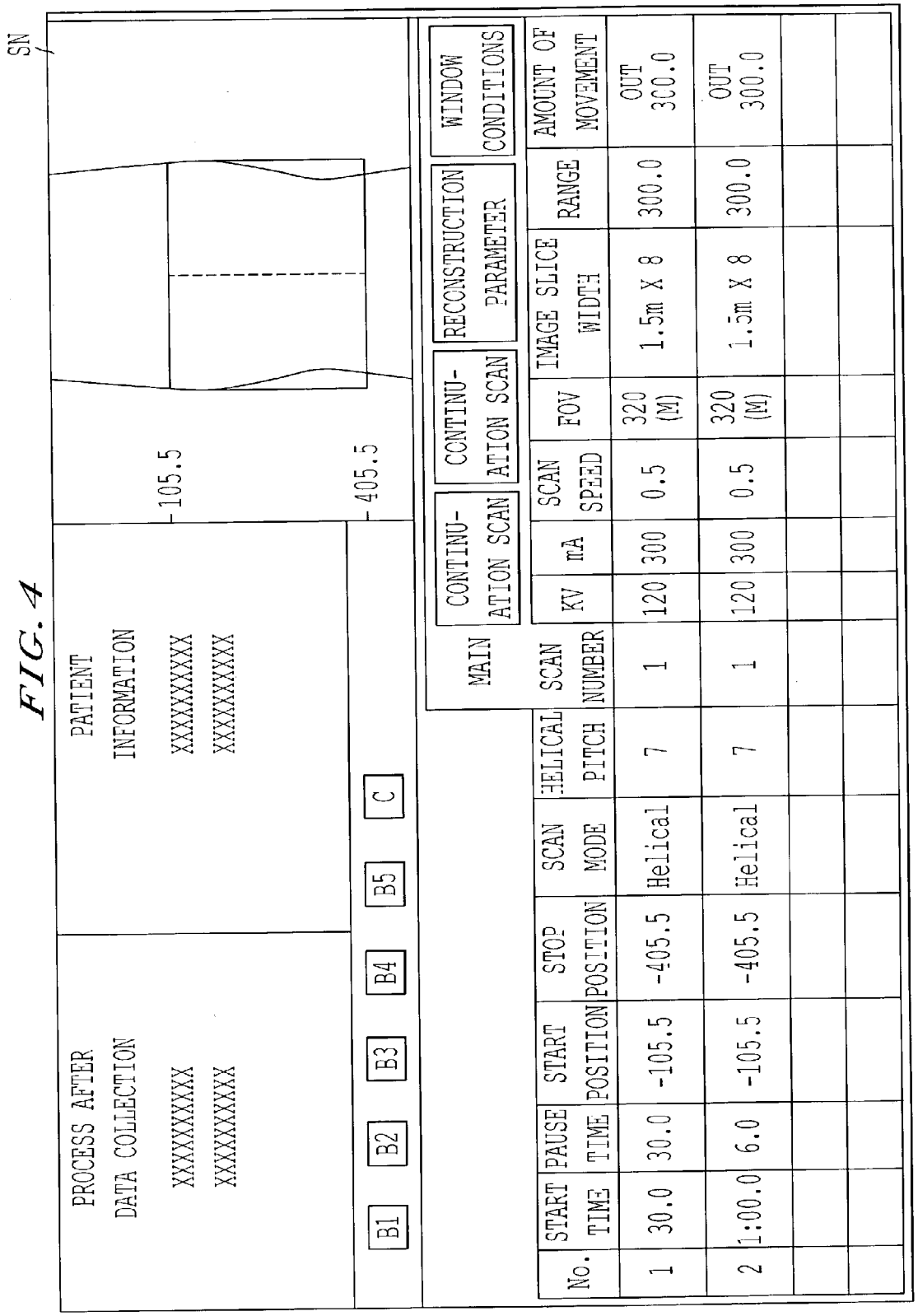
FIG. 4 is an illustration of an example displayed on a monitor.

One example displayed on a monitor when setting the imaging plan is shown in FIG. 4. In this figure, a screen for setting up the scanning conditions is shown. This schedule setting screen is displayed on the monitor of the display 116, however it may be displayed on a monitoring screen of the input unit 115. A scanogram image (SN), created based on the data obtained by moving bed when the X-ray tube and the X-ray detector are not moved, is displayed on the upper right position of this schedule setting screen. A frame for setting up the scanning range on this scanogram image is also displayed. The operator can set all scanning areas (all scanning ranges) by reducing, moving, expanding and rotating the frame. The object (patient) information is displayed on the upper and central part of this schedule setting screen, and a process after the data collection is further displayed on its left. Furthermore, various kinds of buttons which the operator operates if necessary are displayed under the patient information and the process. There are B1 to B5 buttons for priority instructions of the amount of the emitted X-ray to the patient (X-ray dose), scanning time, the total time of scan and reconstruction, quality of image, and X-ray tube OLP (Over Load Protection of the X-ray tube), respectively, and a button C used for confirmation of the operator's intention. Furthermore, a scanning schedule table is displayed at the bottom of this setting screen.

In this scanning schedule table, a plurality of scanning operations are perpendicularly arranged according to the order of a series. The operator makes and arranges using each function, such as a new addition, a copy, and an elimination. In each column, the start time of each scanning operation on the basis of the time when the operator pushes a trigger button, the pause time between scanning operations, the scan start position, the scan stop position, the scan type (the conventional scan (multi-slice scan, single-slice scan)/the helical scan), the helical pitch, and the main buttons are arranged. The main buttons indicates buttons for the number of times of scanning, the tube voltage supplied to the X-ray tube 101 from the high-voltage generating unit, the tube current, the scanning speed (scanning total time), the size of FOV, the image slice width (the thickness of the imaging slice times the number of slices), the scanning range, the amount of movements of the bed after the scan, respectively.

By clicking the button of a reconstruction parameter, as reconstruction conditions, the imaging planning creation system 120 displays the reconstruction method (the fan-beam reconstruction method/the cone-beam reconstruction method), the thickness (reconstruction thickness) of a reconstruction slice, the image generation pitch, the reconstruction size, the reconstruction matrix size, and a threshold which extracts an interested part, for example. Initial recommendation value of each condition is inserted by the imaging planning creation system 120, and the operator can change the value if needed. In addition, the size or the position of the flame on the scanogram image changes automatically when the value of the start position, the stop position, the scanning range, or the size of FOV is changed. If the flame is moved by clicking each value is changed.

Next, the operation of the X-ray CT apparatus in the first embodiment will be explained. The following operation is performed by the operator based on the imaging planning program stored in the subsidiary memory unit 112. The operator inputs information, such as the process after the data collection and the patient information on the screen of the display of the input unit 115 shown in FIG. 4. The operator takes the scanogram image data of the patient by generating the X-ray from the X-ray tube without rotating the X-ray tube and the detector and inserting the bed into the opening space of the gantry. By processing the scanogram image data obtained as described above, the scanogram image can be obtained. This scanogram image SN is described as shown in FIG. 4 on the screen. In FIG. 4, the case where the operator selects the auto filming mode is shown.

Next, the operator sets the flow from the scan to display/record, such as the imaging part of the patient, the scan conditions, the reconstruction conditions, the display/record conditions (window conditions) etc. on the screen according the imaging planning program. The imaging planning creation system 120 prepares the first to third modes in order that the operator can set the conditions easily.

Figure 5:
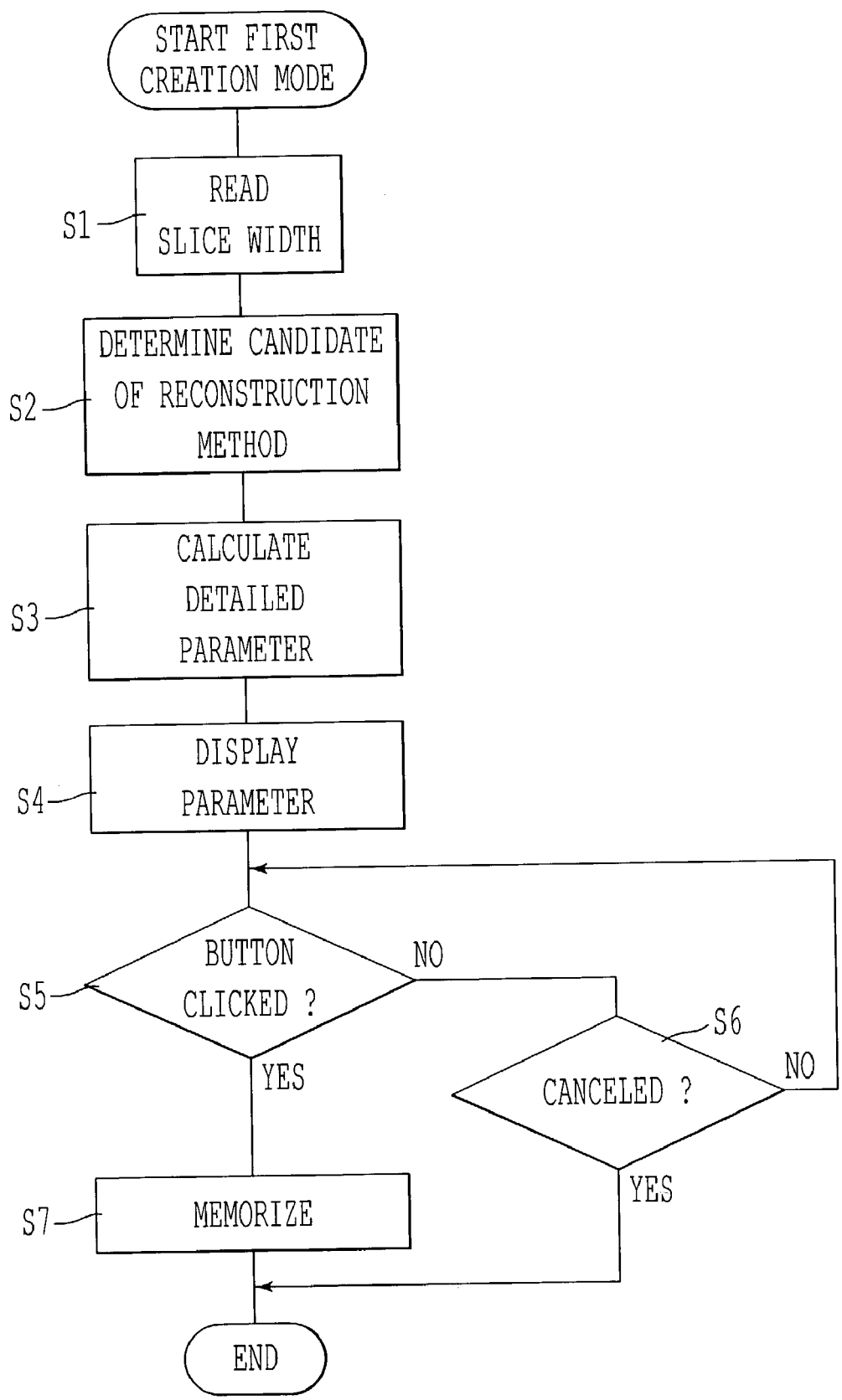
FIG. 5 is a flow chart explaining an operation of the first creation mode in the first embodiment.
Figure 6:
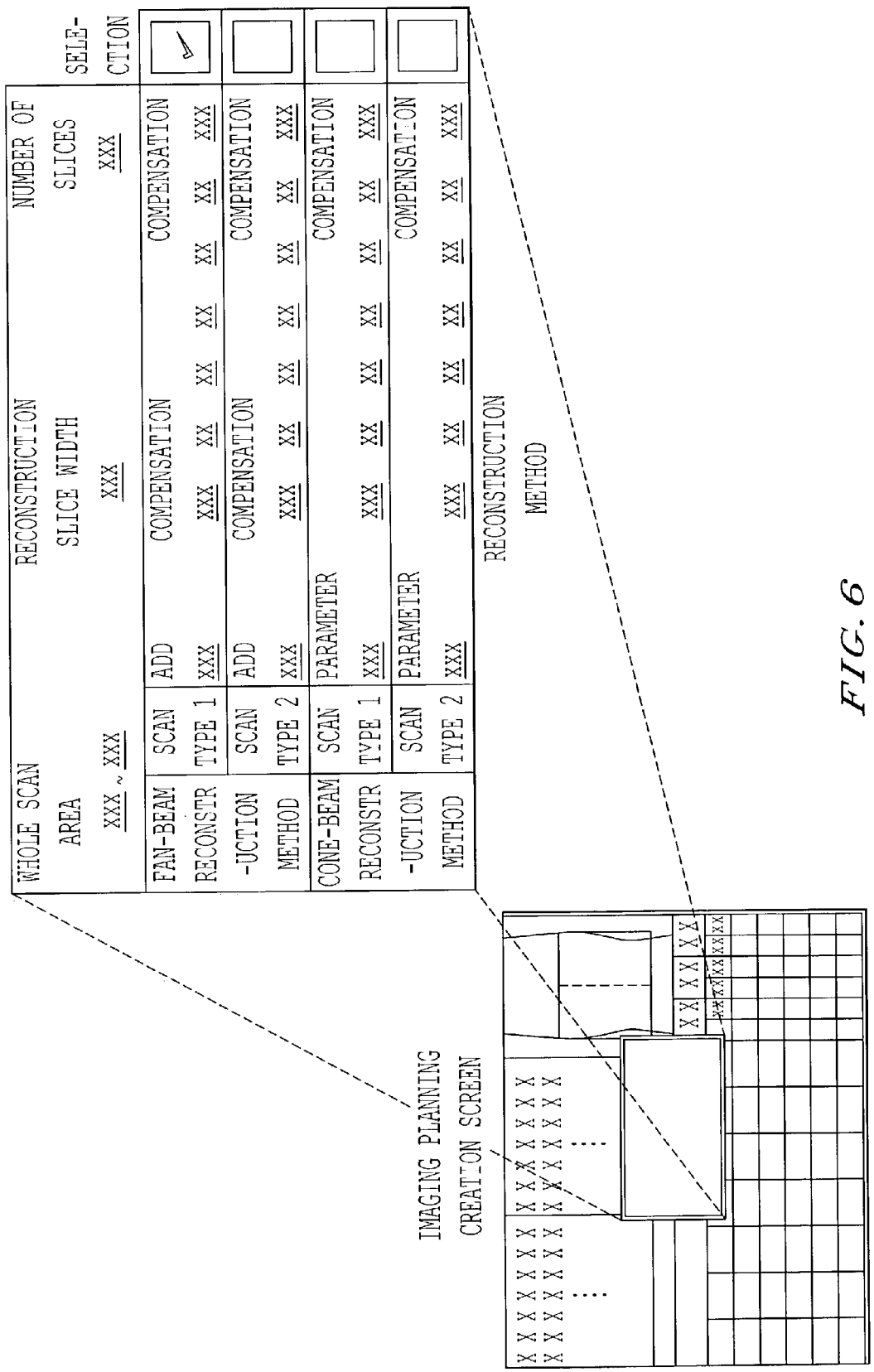
FIG. 6 is an illustration of an example displayed on a monitor in the first creation mode.

The first creation mode is shown in FIGS. 5 and 6. This first creation mode aims at showing the operator the candidate of a possible reconstruction method. The operator finally determines the reconstruction method with its intention with reference to the shown reconstruction method. Specifically, the imaging planning creation system 120 reads the image slice width inputted by the operator (Step 1). The imaging planning creation system 120 determines the candidate of a reconstruction method applicable to the image slice width with reference to the look-up table stored beforehand (Step 2). Thereby, the candidate of one or more reconstruction methods is determined and shown to the operator (presentation). The fan-beam reconstruction method (additional processing before DAS or after DAS is also included) and/or the cone-beam reconstruction method are included in the candidate of these reconstruction methods.

Next, the detailed parameter contained in each determined reconstruction method is calculated in the imaging planning creation system 120 (Step 3). Thus, the reconstruction method and the calculated parameter are displayed (presented) in the imposed mode on the screen, as shown in FIG. 6 (Step 4). According to the image slice width, two kinds of reconstruction methods are listed on this imposed screen, for example. In FIG. 6, as the reconstruction methods the fan-beam reconstruction method (additional processing before DAS or after DAS is also included), and the cone-beam reconstruction method are displayed. Each reconstruction method is subdivided according to the kind of applicable scan types (multi-slice scan, helical scan, etc.). The parameter is displayed for every classification decided by combination of the reconstruction method and the scan types.

In this parameter, the information showing the Feldkamp reconstruction or ASSR reconstruction when the reconstruction method is the cone-beam reconstruction method, and the information showing the helical compensation method when the helical scan is used are also included. Thereby, a series of flow of the multi-slice helical scan, additional processing method before DAS or after DAS, the helical compensation method, the fan-beam reconstruction method (the number of slices is four) is shown. Another series of flow of the multi-slice conventional scan, the length compensation, the cone-beam reconstruction method is displayed. A check button for the operator choosing is displayed on the tail end of each flow of the presentation screen, respectively.

The operator who takes a look at the presentation screen of this reconstruction method chooses a desired combination of the reconstruction method and the scan type by clicking the check button. The imaging planning creation system 120 detects whether the button is clicked or not (Step 5). When it determines NO, namely it is not clicked, it determines whether a setup of the reconstruction method is cancelled or not on the basis of another operation information (Step 6). If it is also NO, the imaging planning creation system 120 recognizes that the operator keeps consideration, then returns the processing of Step 5. While, the judgment of Step 6 is YES, since it is recognized to be cancelled and it ends processing. In Step 5, if it detects YES, since it means one of combinations of the reconstruction method and the scan type is chosen, the selected reconstruction method is memorized in the memory unit 111, and the processing is ended (Step 7).

Figure 7:
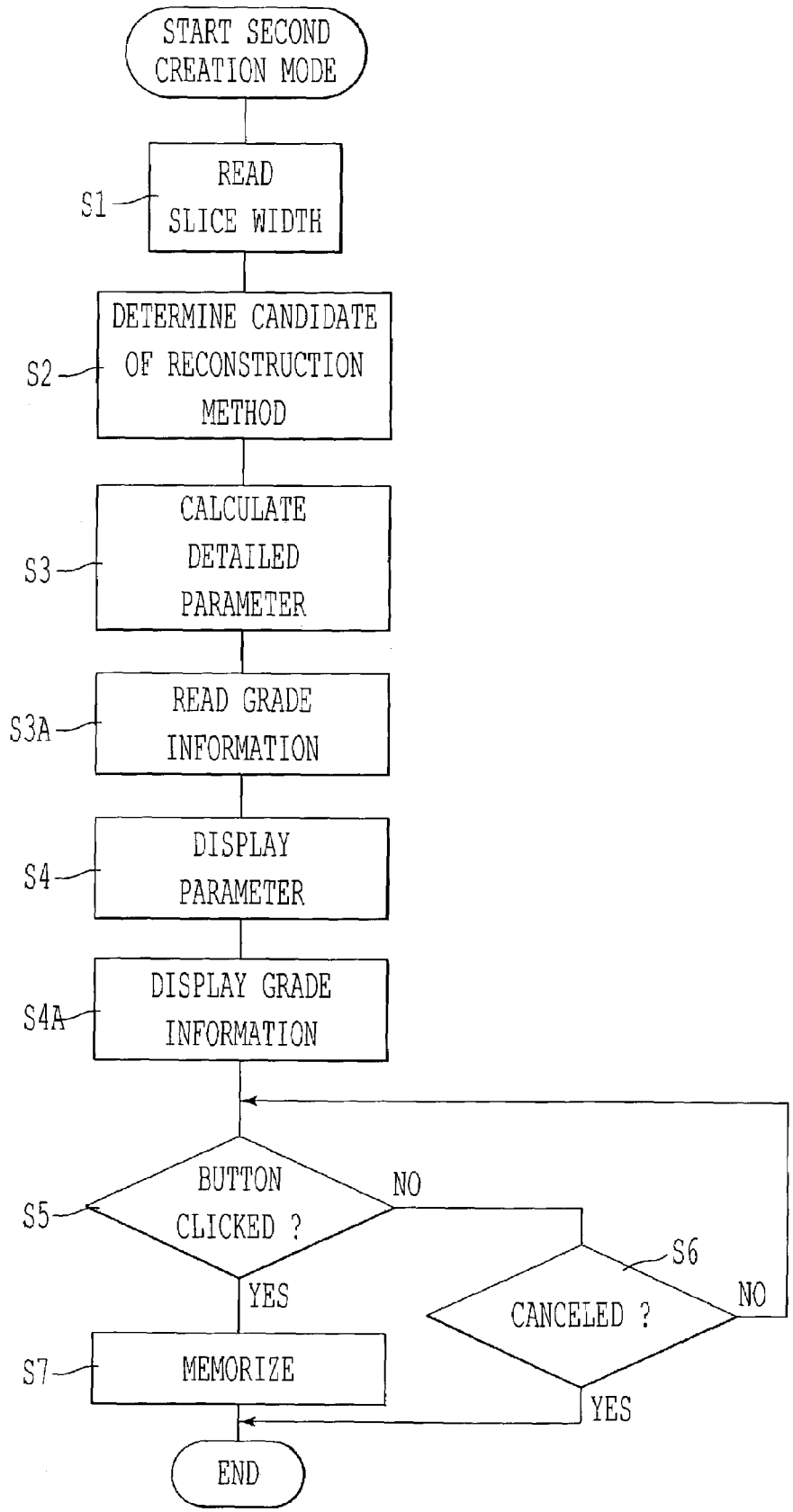
FIG. 7 is a flow chart explaining an operation of the second creation mode in the first embodiment.
Figure 8A:
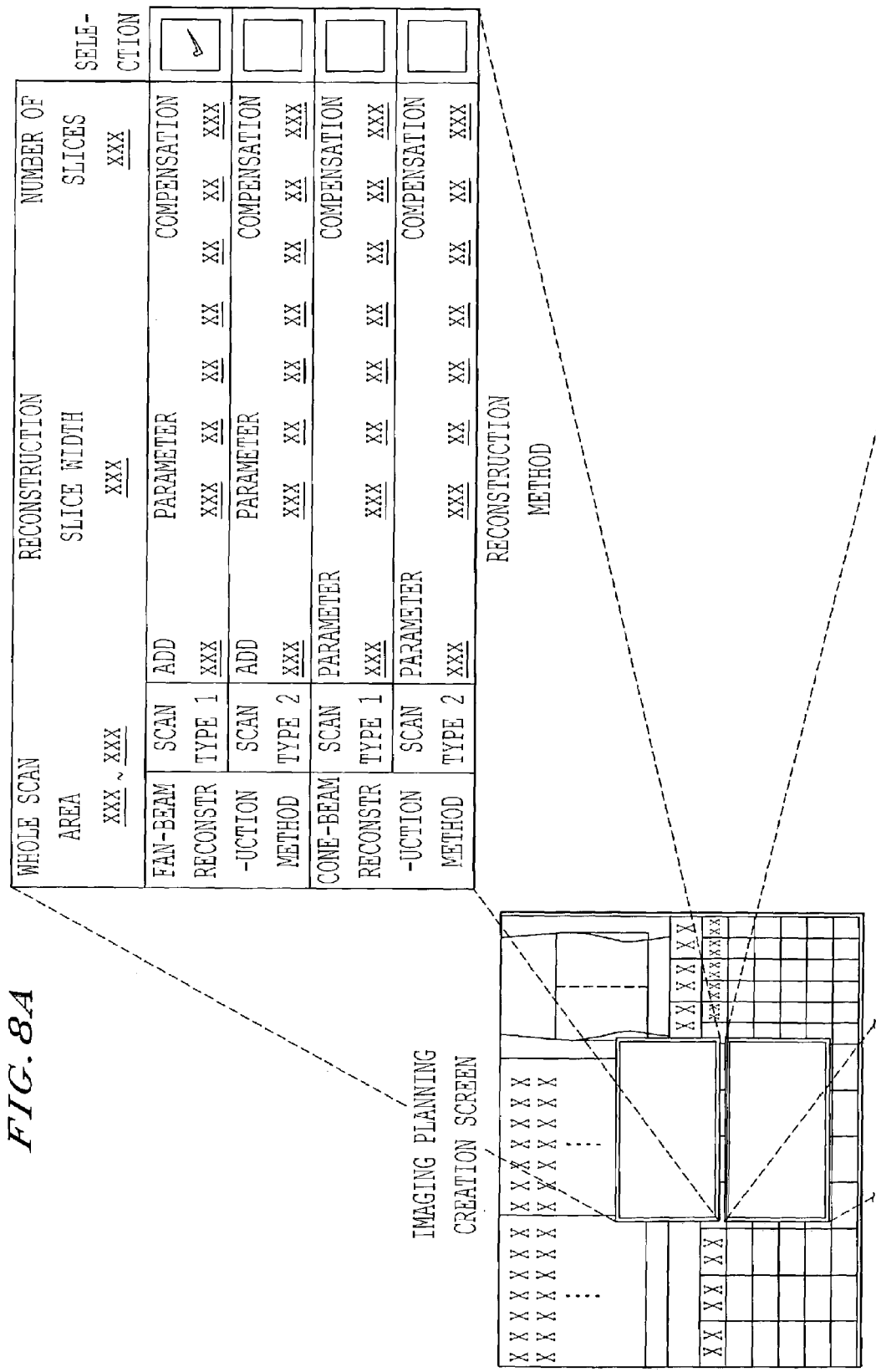

The second creation mode is shown in FIGS. 7, 8A and 8B. The second creation mode presents the grade information on each reconstruction method in addition to the reconstruction method shown in the first creation mode mentioned above. The only grade information may be displayed. In order to show this grade information, the imaging planning creation system 120 performs the processing shown in FIG. 7. This processing adds step 3A and 4A to the processing of FIG. 5 in the first embodiment.

In step 3A, the grade information on a reconstruction method is read from the grade information table stored beforehand according to one or more reconstruction methods determined at Step 2. This read grade information is imposed on the screen in list form as shown in FIGS. 8A and 8B (Step 4A). The grade information in FIGS. 8A and 8B is evaluated in the cases of the fan-beam reconstruction method (the number of slices is four) and the cone-beam reconstruction method (the number of slices is eight) by each item, such as the X-ray dose, the scanning time, the total time from the scan to the reconstruction, quality of image (low contrast/high contrast), and X-ray tube OLP (scanning waiting time). In FIGS. 8A and 8B, the character of "E" shows excellent in comparison with the other reconstruction method, and the character of "B" shows bad vice versa. Instead of E or B, other marks, such as circle mark, triangle mark, and X mark.

The X-ray dose is related to the size of the imaging where data is collected. When the image slice width is thick, the cone-beam reconstruction method is better (the X-ray dose is low) than the fan-beam reconstruction method. While, the fan-beam reconstruction method is better (the X-ray dose is low) than the cone-beam reconstruction method, if the image slice width is thin. With regard to the scanning time, since the detector includes many detection segments, the cone-beam reconstruction method is better (short) than the fan-beam reconstruction method, generally. On the other hand, about the total time from the scan to the reconstruction, the fan-beam reconstruction method is better than the cone-beam reconstruction method, when image slice width is thick. About the quality of image, the cone-beam reconstruction method is better, and about the X-ray tube OLP, the cone-beam reconstruction method is better.

As described above, in the second creation mode, in addition to presentation of one or more reconstruction methods, the grade information is shown by item showing the typical feature of each reconstruction method. In addition, if the only grade information is shown, Steps 3 and 4 are removed among the steps in FIG. 7.

Thus, in the first and second creation modes, according to the image slice width which the operator gives on the imaging planning creation screen, the candidate of the reconstruction methods and its parameter information, and/or the grade information on each reconstruction method are shown automatically. Since important information for the determination of the reconstruction method is immediately acquired on the screen, it becomes easy for the operator to decide the suitable reconstruction method. Therefore, even a novice operator can make an excellent imaging plan, the time for it can be vastly shortened, and the operation of the operator can be efficient. In addition, the burden on the operator is reduced, and the patient processing efficiency is improved. Thus, setting mistake of the imaging plan etc. can be prevented and the accurate and reliable imaging plan can be created.

Figure 9:
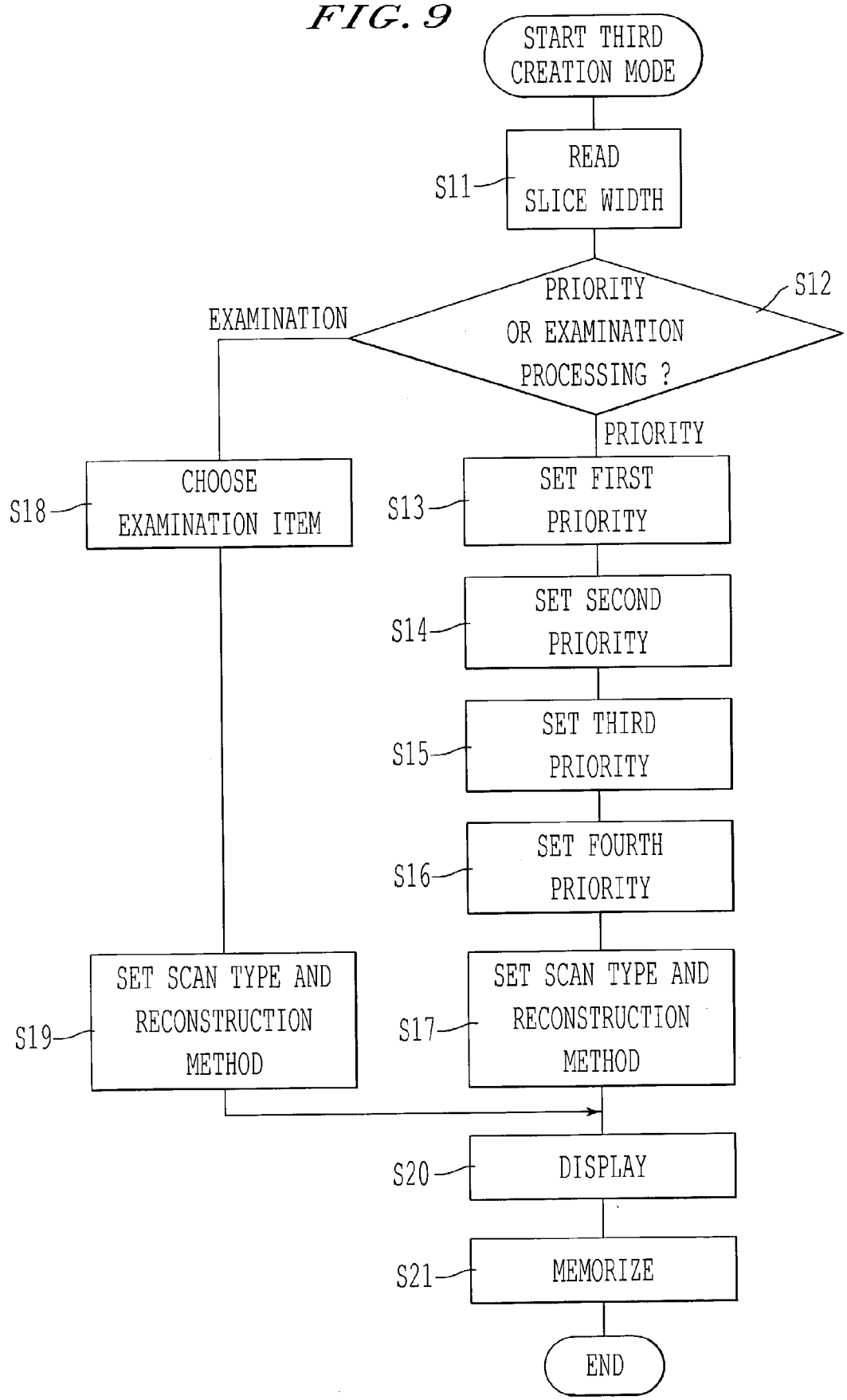
FIG. 9 is a flow chart explaining an operation of the third creation mode in the first embodiment.

Next, the third creation mode will be explained with reference to FIG. 9. As for the third creation mode, the imaging planning creation system 120 sets up the scan type and the reconstruction method automatically. The imaging planning creation system 120 performs a series of processing shown in FIG. 9. The imaging planning creation system 120 reads the image slice width set by the operator (Step 11). The imaging planning creation system 120 judges whether "priority processing" or "examination processing" is performed based on operation information from the operator (Step 12). Here, the "priority processing" is processing which sets the reconstruction method according to the order of priority among items which shows the typical feature of each reconstruction method, such as the X-ray dose, the scanning time, the total time from the scan to the reconstruction, quality of image (low contrast/high contrast), and one or more of the X-ray tube OLP (scanning waiting time). This ordering is set by the operator. The "examination processing" is processing which sets the reconstruction method according to the instructions from the operator about the above-mentioned items, such as the scanning time, the total time, quality of image, and the X-ray tube OLP.

If the priority processing is selected by the operator at step 12, the imaging planning creation system 120 sets the first priority (for example, the X-ray dose), the second priority (for example, the scanning time), the third priority (for example, the total time), and the forth priority (for example, quality of image) through Steps S13 to S16 according to the input from the operator. In this case, the X-ray tube OLP remains (set as the fifth priority). Only the first priority may be made or the first to the third priority may be set, as another example.

After the priority is set, the imaging planning creation system 120 searches the stored reference table according to the priority information, sets the optimum scan type and the reconstruction method (Step 17). On the other hand, when the "examination processing" is selected by the operator at Step 12, the imaging planning creation system 120 shifts to Step 18, and chooses at least one of examination items (for example, the scanning time) according to the input from the operator. Also in this case, the imaging planning creation system searches the reference table according to the examination information, and determines the optimum scan type and the reconstruction method (Step 19). The scan type and the reconstruction method according to the image slice width are displayed, for example imposed, on the imaging planning creation screen (Step 20). The information on this scan type and the reconstruction method are stored in the memory unit 111 (Step 21).

Thus, in the third creation mode, since the optimum scan type and reconstruction method are set automatically according to the image slice width the operator inputs, the burden on the operator can be reduced. Moreover, failure of making the imaging plan is also prevented, even if a novice operator makes it.

The imaging plan is interactively formed between the imaging planning creation system 120 and the operator through the set of the above scan type and the reconstruction method. Two or more parameters related with the selected imaging plan, such as the signal collection, image creation, and the image display are loaded to the host controller 110. After the operator orders the imaging start, the signals are collected according to the loaded the signal collection parameter, the image is reconstructed according to the loaded the reconstruction parameter, the image is displayed or recorded according to the loaded image display or record parameter, and the image is filmed according to the loaded window conditions.

Figure 10:
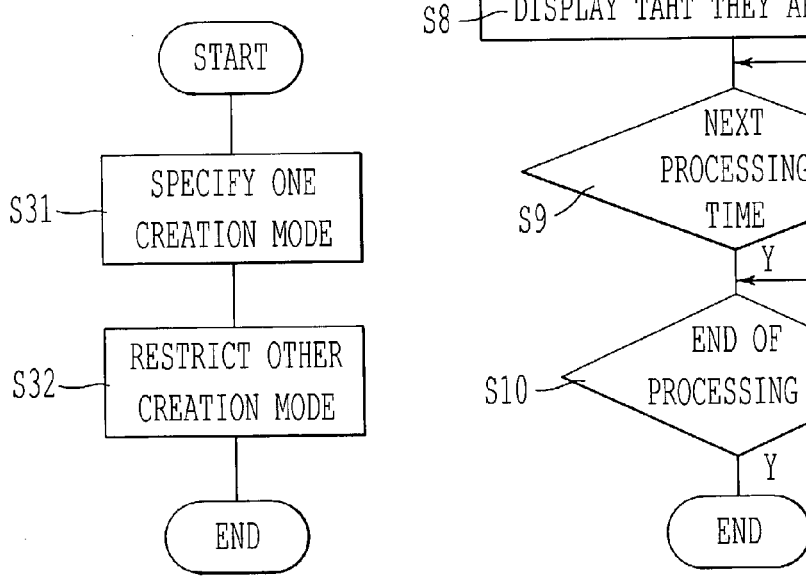
FIG. 10 is a flow chart explaining an operation of a modified creation mode for restricting one mode among three modes in the first embodiment.

Moreover, a modification of the above-mentioned first to third creation modes is shown in FIG. 10. Although the creation mode can be selected by the operator in the above-mentioned embodiment, in this modification, the creation mode can be restricted to one. In this modification, at the time of installation of the multi-slice X-ray CT apparatus, the one creation mode to use is decided, and a serviceman restricts other creation modes in the memory unit 111 (the first to third creation modes are installed in advance) (FIG. 10, Steps 31 and 32).

Thus, the same X-ray CT apparatus can be used in different ways, the second creation mode in Japan and the third creation in the U.S., for example. In addition, the image slice width can be set up in consideration of the limit of the image slice width by which a cone angle influences quality of image. The number (the number of segments of DAS) of slices can be changed to not only in four but also suitable number like one or two in the fan-beam reconstruction method, and can be changed to not only eight but also other number, 16, 32, or 64, for example. In addition, the DAS 104 uses two segments in the fan-beam reconstruction method, and four segments can be used in the cone-beam reconstruction method.

The present invention is not limited to the above embodiment, and various modifications may be made without departing from the spirit or scope of the general inventive concept. For example, although the number of segments of the DAS in the body axis direction is switched to eight segments or four segments etc. according to the reconstruction algorithm or the image slice width in the above embodiment, the number of the segments may be fixed to a predetermined number (for example, eight segments). In this case, the number of slices can be selected, four or eight, for example, in a reconstruction parameter sheet. Thereby, the operator can save the time to choose the number of slices of scanning conditions in the imaging plan.

Moreover, in the above-mentioned embodiment, although the X-ray CT apparatus 100 itself executes data processing like the reconstruction processing, cross-sectional conversion processing and display processing, instead of this, the external image processing unit 200 shown in FIG. 1 may performs the processing. In this case, the data may be transmitted from the X-ray CT apparatus 100 to the external image processing unit 200, before the reconstruction, after the reconstruction or just before the display.

Moreover, in the above-mentioned embodiment, although ROTATE/ROTATE type where an X-ray tube and a detector rotate around the patient is explained, (STATIONARY/ROTATE) type where the array of many detection elements are arranged as the shape of a ring and the only an X-ray tube rotates around the patient may be used. Moreover, although the case where the about 360 degrees projection data around the patient is used for the reconstruction is explained in the above embodiment, any reconstruction algorithm like a half scan where 180 degree and view angle projection data may be used. Furthermore, although the above-mentioned embodiment explains the indirect conversion type detector where the X-ray changes into the light with the scintillator and the light is converted to into an electric charge with light-electronic conversion elements, such as a photo-diode, the direct type detector where the X-ray directly changes to an electric charge with the semiconductor material where the electron hole pair is generated and moves each side may be used. Moreover, in the above-mentioned embodiment, although one X-ray tube type X-ray CT apparatus is explained, two or more pairs of an X-ray tube and an X-ray detector, so-called multi X-ray tube type X-ray CT apparatus may be used.

As explained above, even the operator who is not skilled can set the appropriate reconstruction method easily, and the imaging plan can be made easily and quickly without the much burden of the operator.

Next, the second embodiment according to the present invention is explained with reference to FIGS. 11 to 21. Although, in the first embodiment, especially the reconstruction method is explained, the second embodiment is related with the helical pitch, etc. of the multi-slice CT apparatus. The second embodiment is different from the first embodiment in the imaging planning program stored in the subsidiary memory unit 112.

Figure 11:
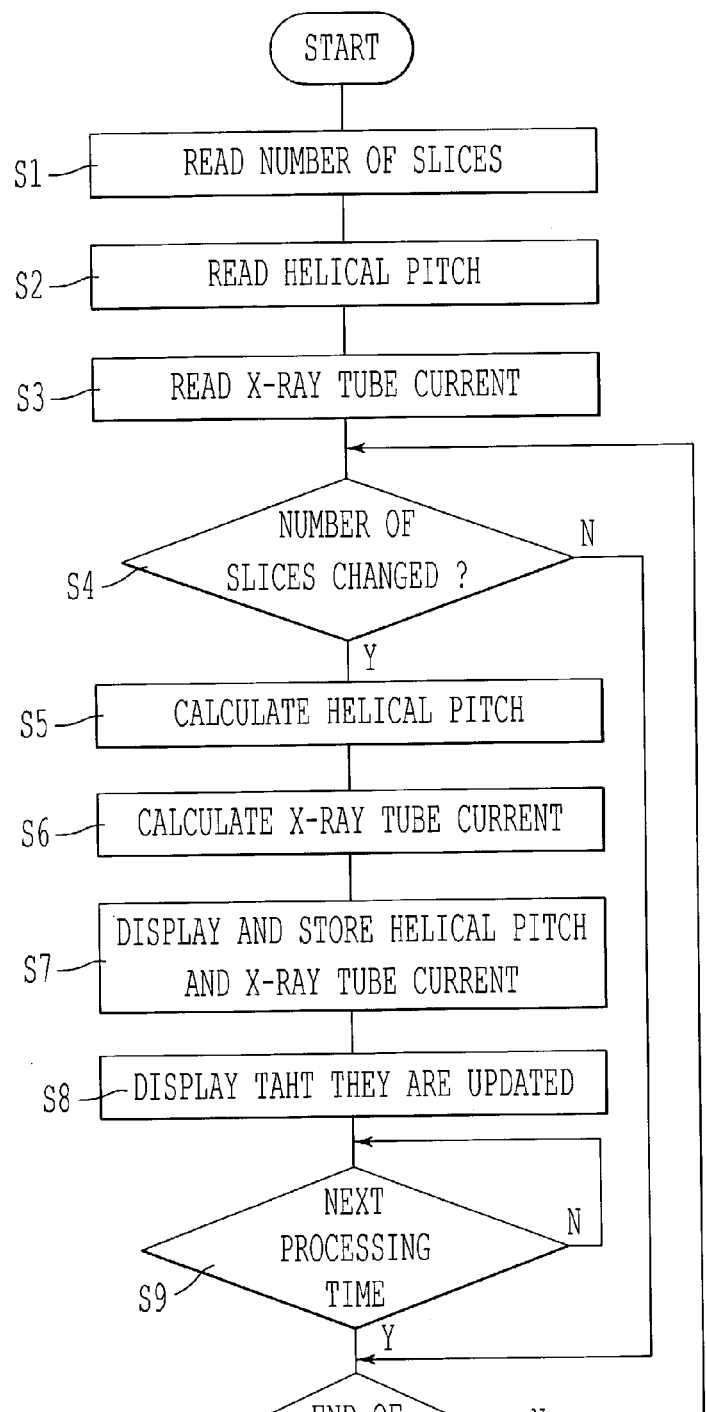
FIG. 11 is a flow chart explaining an operation of the second embodiment.

In the first example according to the second embodiment, the helical pitch, etc. is automatically displayed on the basis of the information inputted by the operator. The operation of this first example is explained. The operator inputs predetermined information, such as the patient information and the process information after the data collection, on the imaging planning creation screen, shown in FIG. 4, displayed on the display 116 of imaging planning creation system 120. Subsequently, the operator takes a scanogram image data of the patient. Predetermined processing is performed to the scanogram image data, and the scanogram image SN is obtained. This scanogram image SN is displayed as shown in FIG. 4 on the imaging planning creation screen. In FIG. 4, the case where the operator selects the auto filming mode is shown. Next, the operator sets the flow from the scan to the display/record, such as the imaging part of the patient, the scan conditions, the reconstruction conditions, the display/record conditions (window conditions) etc. on the screen according the imaging planning program. In this case, the assistant processing shown in FIGS. 11 and 12 automatically executed by the X-ray CT apparatus. The assistant process starts according to the start of the imaging planning process (main process) and runs in the background of the imaging planning process by the host controller 110 which is the central part of the imaging planning creation system 120. Therefore, the operator can be assisted and concentrate on making the imaging plan without considering such assistant process. FIG. 11 shows the assistant process when the number of the used segments of the X-ray detector 103, namely the number of slices, is changed in the middle of the imaging planning creation processing mentioned above. In detail, the host controller 110 reads the number (the number of detector element segments) of slices specified, the helical pitch, and the tube current (Steps 1 to 3). The host controller 110 judges whether the number of slices is changed in the imaging planning creation processing (Step 4). Since the host controller 110 watches the inputted value to the window (refer to FIG. 4) of the image slice width on the imaging planning creation screen with the input unit 115, the above-mentioned change can be checked based on the change of this value.

When it is judged YES which means the number of the slices is changed in Step 4, the host controller 110 calculates the appropriate helical pitch according to the number of change slices (Step 5). The calculated helical pitch may be proportionate to the number of the changed slices, may be proportionate and approximate to the changed number, or may be proportionate to the changed number and shifted to the high-density sampling by 0.5 pitches. For example, in the case of proportion, if the operator changes the slice number (the number of detection segments) to 8 after it is set that the slice number is 4 and the helical pitch is 5, the helical pitch is automatically changed into 10. In addition, after the slice number is set 8 and the helical pitch is 7, the slice number changes into 4, then the helical pitch is automatically changed to 3.5.

The host controller 110 calculates the tube current supplied to X-ray tube 101 according to the number of changed slices (Step 6). For example, after it is set the slice number is 4 and the helical pitch is 5, if the slice number is changed to 8, the tube current is automatically changed into a half. Thereby, the X-ray dose is kept equivalent. The host controller 110 updates the helical pitch and the tube current calculated at Steps 5 and 6 on the display and stores them (Step 7). Furthermore, the updated information is automatically displayed (Step 8), for example, the updated helical pitch and the tube current may be blinked for a predetermined period of time or the message indicates the change may be displayed. Then, the host controller 110 waits for a predetermined period of time, and it detects the next processing timing, and the step is back to the Step 4 unless it is ordered in an end of processing (Steps 9 and 10).

Figure 14:
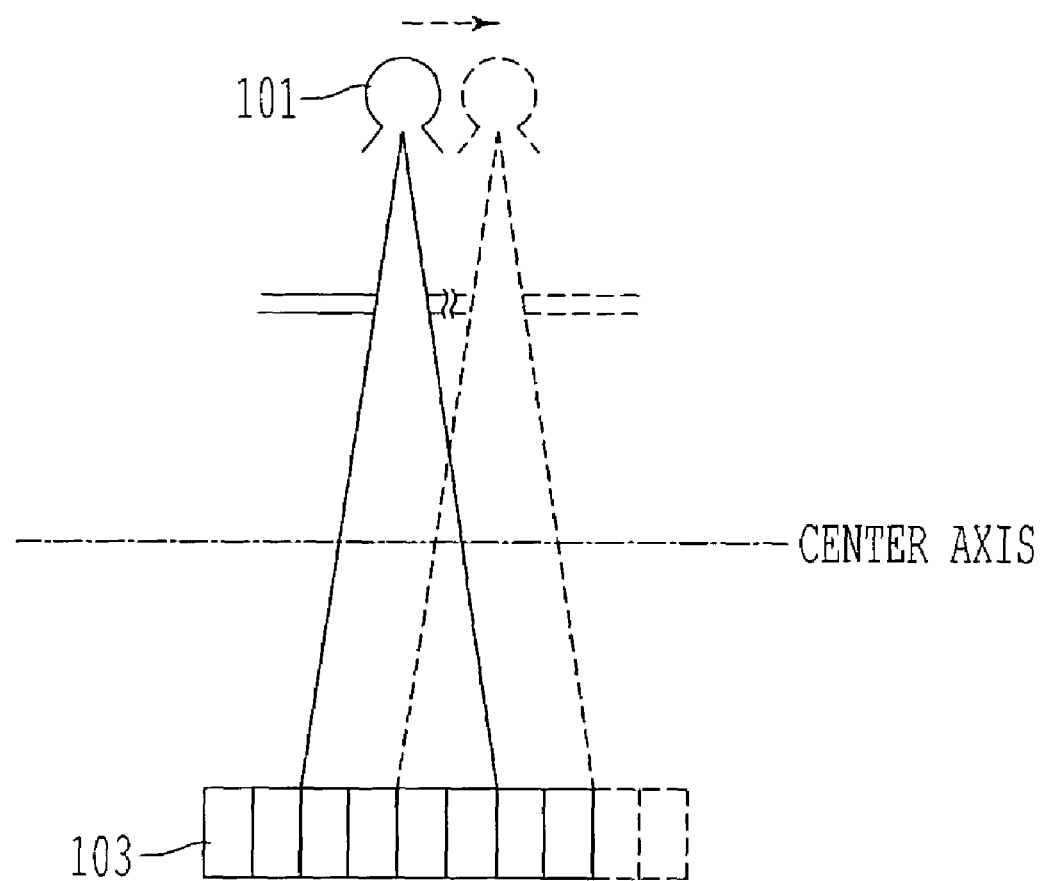
FIG. 14 is an illustration explaining an operation at the time of scan.
Figure 16:
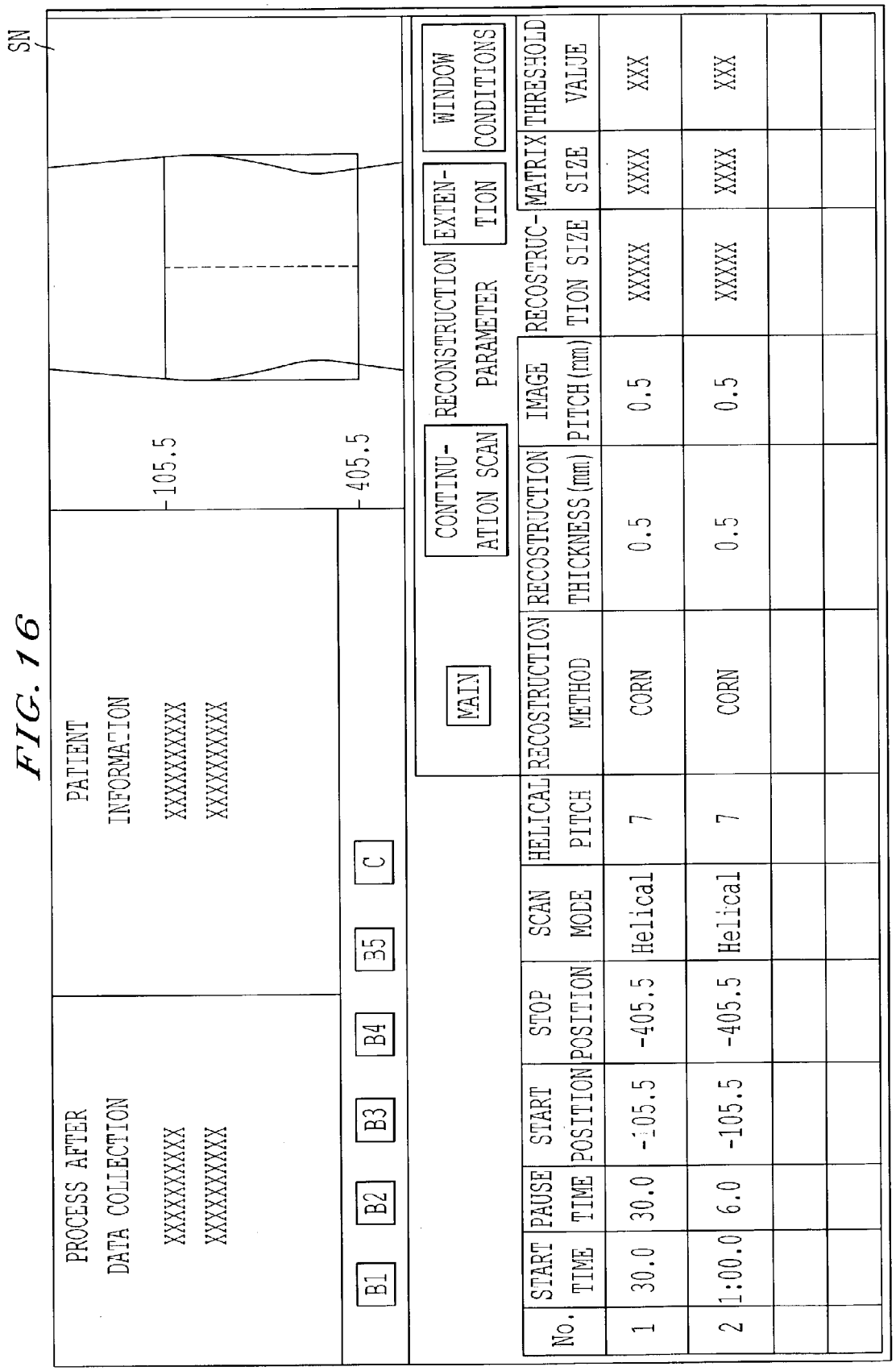
FIG. 16 is an illustration of an example displayed on a monitor in the first modification of the second embodiment.

Although both of the helical pitch and the tube current are changed automatically in processing of FIG. 11 as mentioned above, only one of them may be performed. As one example where the only helical pitch is changed, after it is set that the slice number is set 8 and the helical pitch is 7, the slice number changes into 4. In this case, the helical pitch is automatically changed into 3.5 which is half value by processing of FIG. 11 mentioned above. After the operator confirms this change, the updated value is used for the scan. The state of the X-ray after changing is shown in FIG. 14.

As one example where the only tube current is changed, after it is set that the slice number is set 4 and the helical pitch is 5, the slice number changes into 8. In this case, the tube current is automatically changed from 120 mA to 60 mA which is half value by processing of FIG. 11. In this case, the helical pitch keeps 5.

Figure 12:
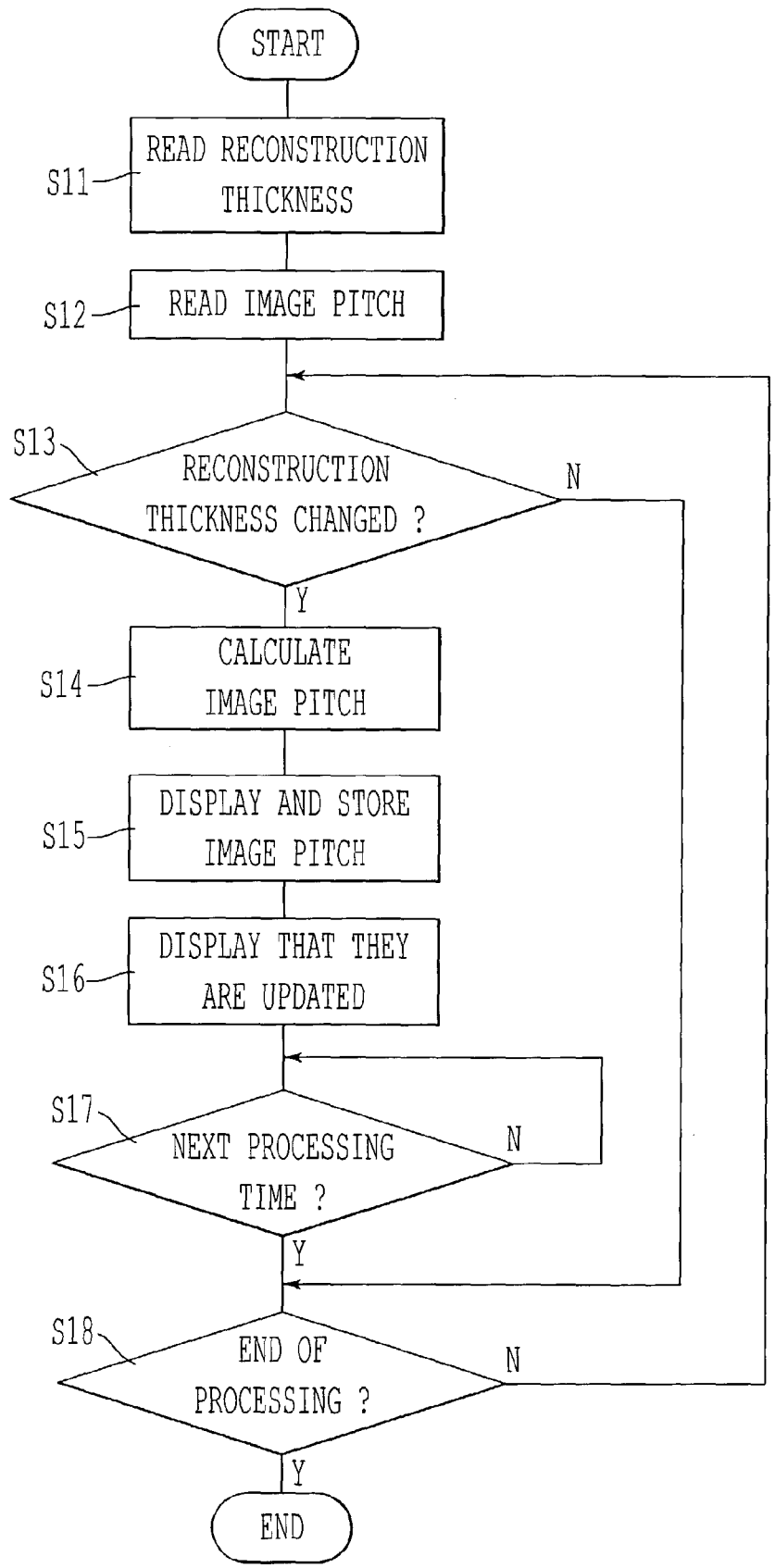
FIG. 12 is a flow chart explaining an operation of the first modification of the second embodiment.

Next the case where the reconstruction thickness is changed is explained with reference to FIG. 12. The host controller 110 reads the reconstruction thickness of the imaging slice and the image pitch (Steps 11 and 12). The host controller 110 judges whether the reconstruction thickness is changed in the imaging planning process (Step 13). Since the host controller 110 watches the inputted value to the window (refer to FIG. 15) of the reconstruction thickness on the imaging planning creation screen with the input unit 115, the above-mentioned change can be checked based on the change of this value.

When it is judged YES which means the reconstruction thickness is changed in Step 13, the host controller 110 calculates the appropriate image pitch according to the reconstruction thickness (Step 14). In this calculation, the image pitch which is proportionate to the changed reconstruction thickness is obtained. For example, although the reconstruction thickness is set 1 mm and the image pitch is 1 mm once, the reconstruction thickness is changed to 0.5 mm, then the image pitch is automatically changed into 0.5 mm. The host controller 110 updates the reconstruction thickness calculated at Steps 14 on the display and stores it (Step 15). Furthermore, the updated information is automatically displayed (Step 16), for example, the updated reconstruction thickness may be blinked for a predetermined period of time or the message indicates the change may be displayed.

Figure 17:
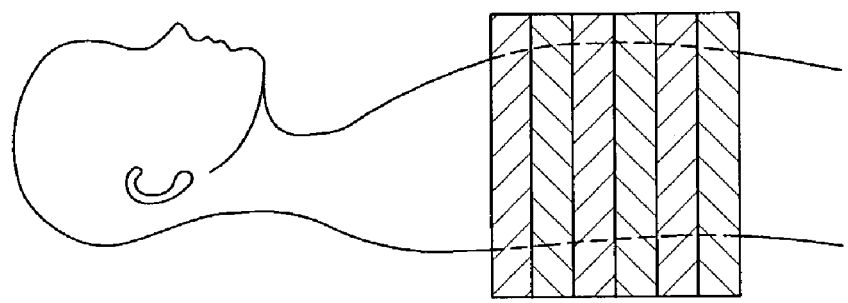
FIG. 17 is an illustration explaining an operation at the time of scan.

Then, the host controller 110 waits for a predetermined period of time, and it detects the next processing timing, and the step is back to the Step 13 unless it is ordered in an end of processing (Steps 17 and 18). As one example, although the reconstruction thickness is set 1 mm and the image pitch is 1 mm once, the reconstruction thickness is changed to 0.5 mm, then the image pitch is automatically changed into 0.5 mm. In this case, the displayed image pitch on the imaging planning creation screen is changed from FIG. 15 to FIG. 16. After the operator confirms this change, the updated value is used for the scan. The state of image pitch and the reconstruction thickness are shown in FIG. 17. Thus, even if the reconstruction thickness is changed, images can be reconstructed with no gaps. In the above-mentioned example, although it is set that reconstruction thickness is 1 mm and the image pitch is 1 mm, the thickness can be changed to 2 mm. In this case, the image pitch is also automatically changed into 2 mm.

As mentioned above, in the first example of the second embodiment, when making the imaging plan with the using the multi-slice helical CT apparatus, even if the number of the slices or the image thickness is changed, the parameter which relates to the number of slices or the image thickness (the helical pitch, the tube current and the image pitch) can be automatically changed.

Therefore, since it can prevent the operator from missing changing the parameter, and also from obtaining the low quality of image because of the missing. Moreover, since the re-imaging due to such a cause is not necessary, the X-ray dose can be reduced. Furthermore, since the operator may not watch and change the related parameter manually, the burden of the operator can be reduced and the patient throughput can be improved.

Figure 18:
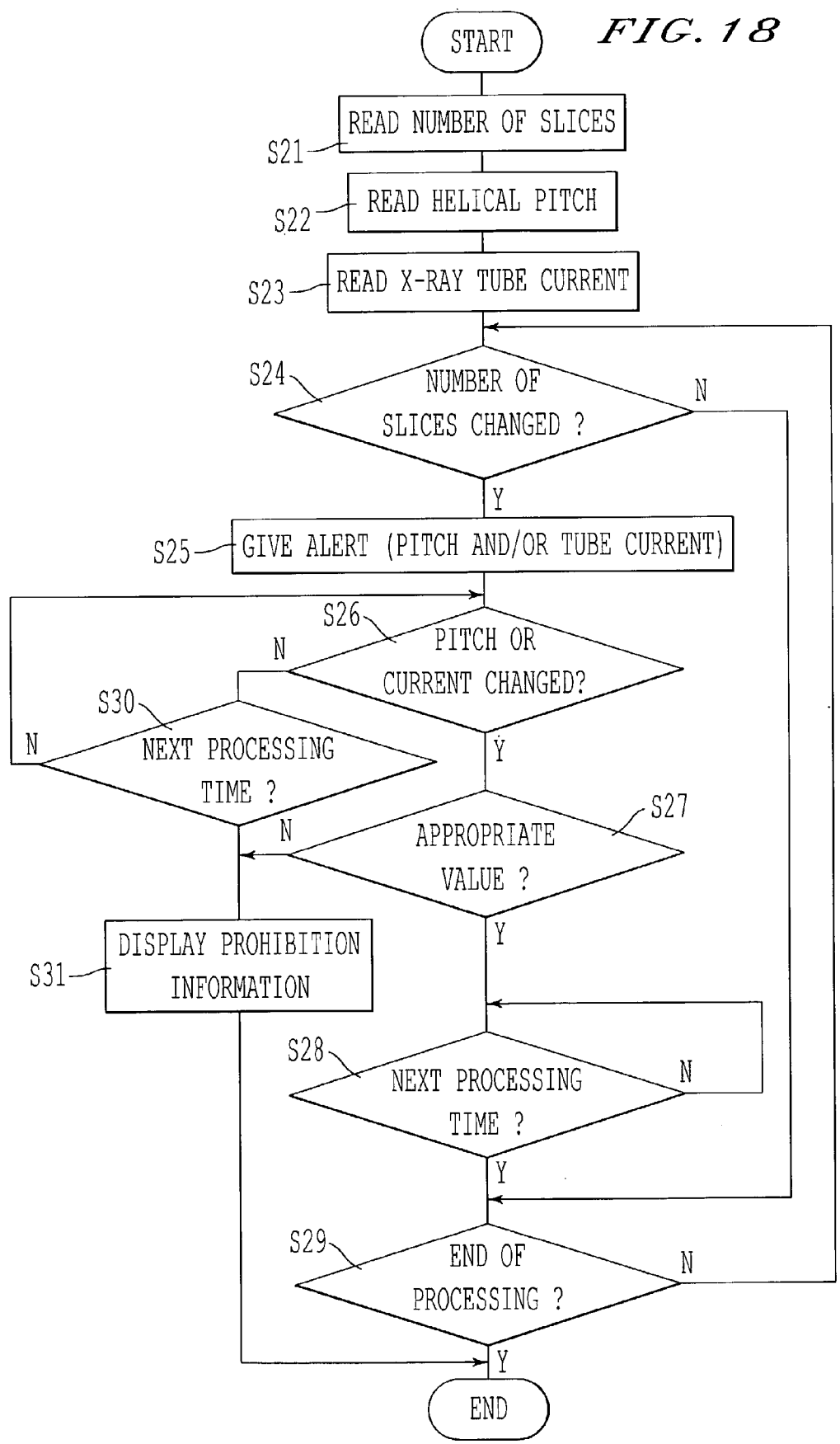
FIG. 18 is a flow chart explaining an operation of the second modification of the second embodiment.

The second example of the second embodiment will be explained with reference to FIGS. 18 and 19. In the following explanation, the same mark is used for a thing the same as that of the first embodiment, and the explanation is omitted or simplified. FIG. 18 shows the alert (warning) processing at the time of changing of the number of the detector element segments, namely the number of slices, of the X-ray detector 103 in the middle of the imaging planning creation processing mentioned above. Specifically, the host controller 110 performs Steps 21 to 24 which are the same processing as Steps 1 to 4 in FIG. 11 mentioned above. In Step 24, if it is judged that the number of slices is changed into another value, the host controller 110 displays, on the imaging planning creation screen, the alert (warning) information which urges the operator to confirm the value of the helical pitch and/or the tube current that are relevant to the number of slices (Step 25).

This warning is performed in various kinds of modes, such as changing the background color of the window of the helical pitch and/or the tube current, blinking the value of the helical pitch and/or the tube current, generating a sound with it, and displaying a pop-up message, as shown in FIG. 19. The example shown in this FIG. 19 shows that the number of slices is set 8 and the helical pitch is set 7 at the beginning for the helical scan, but the operator changes the number of slices to 4, then the background color of the window of the helical pitch and/or the tube current is changed into a conspicuous color in order to urge the operator to check the changed. After the alert, the host controller 110 judges whether the value of the helical pitch and/or the tube current is changed by the operator or not (Step 26). Subsequently, in a certain period of time, if such value is changed, the host controller 110 judges the value is appropriate or not with reference to a table, for example (Step 27).

If the value is appropriate, it stands by to next processing timing, and processing is returned to Step 24 (Steps 28 and 29). On the other hand, if it is judged that the value of the helical pitch and/or the tube current is not changed in Step 26, it stands by further, repeating the judgment for a certain period of time (Step 30). If the value of the helical pitch and/or the tube current is not changed for the certain period of time, scanning prohibition processing for forbidding the helical scan is performed (for example, a prohibition flag is stood) and the prohibition information is displayed on the imaging planning creation screen (Step 31).

Since the operator is urged to change the helical pitch and/or the tube current according to the changed number of slices in the middle of making the imaging plan, the imaging conditions can be set certainly and it is enabled to suppress the degradation of quality-of-image or the increase of the X-ray doze.

Figure 20:
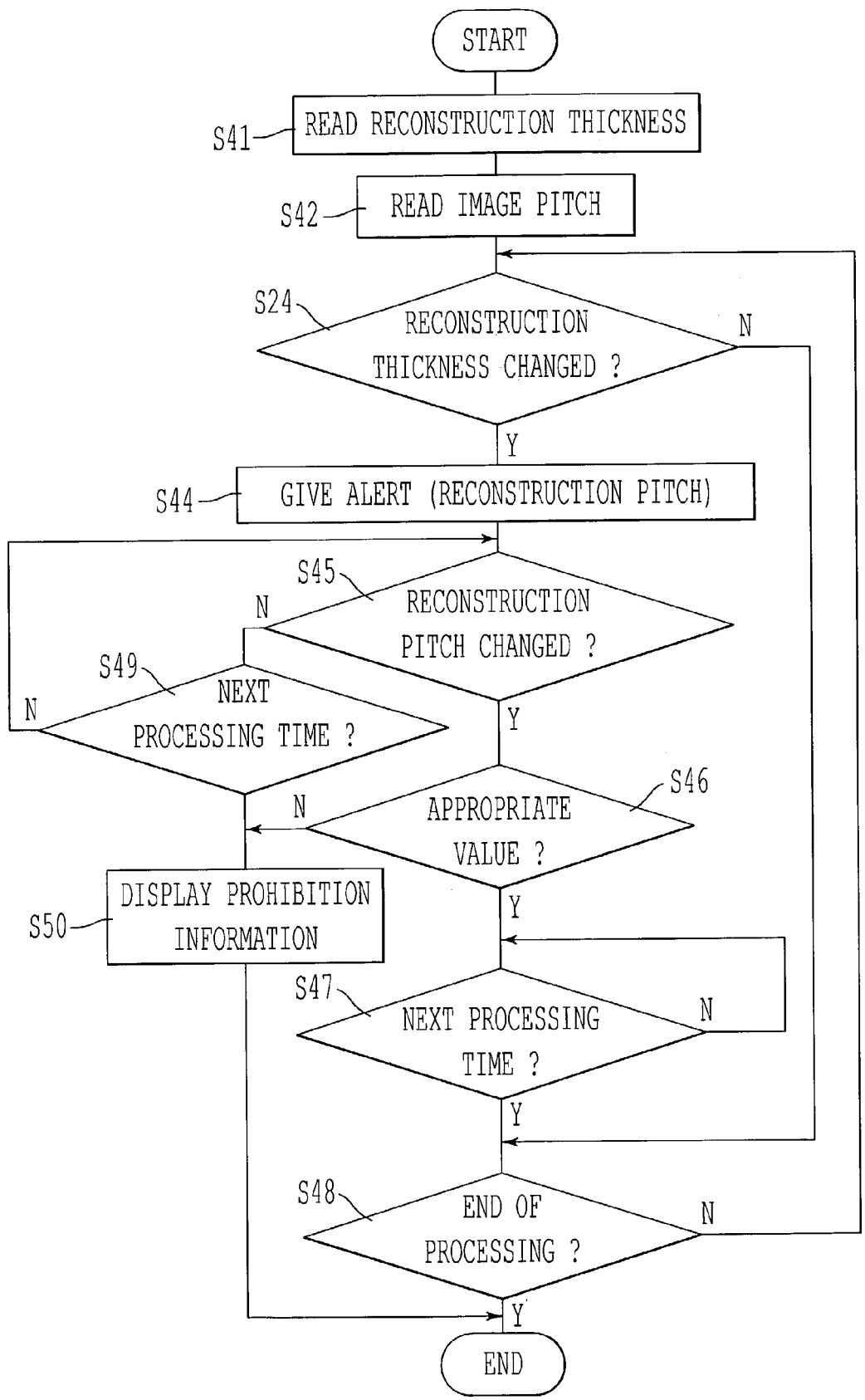
FIG. 20 is a flow chart explaining an operation of the third modification of the second embodiment.

Next, the third example of the second embodiment will be explained with reference to FIGS. 20 and 21. FIG. 20 shows the alert (warning) processing at the time of changing the reconstruction thickness of the image in the middle of the imaging planning creation processing mentioned above. Specifically, the host controller 110 performs Steps 41 to 43 which are the same processing as Steps 11 to 13 in FIG. 12 mentioned above. In Step 43, if it is judged that the reconstruction thickness is changed into another value, the host controller 110 displays, on the imaging planning creation screen, the alert (warning) information which urges the operator to confirm the value of the image pitch that is relevant to the reconstruction thickness (Step 44).

This warning is performed in various kinds of modes, such as changing the background color of the window of the reconstruction thickness, blinking the value of the reconstruction thickness, generating a sound with it, and displaying a pop-up message, as shown in FIG. 21. The example shown in this FIG. 21 shows that the reconstruction thickness is set 1 mm and the image pitch is set 1 mm at the beginning for the helical scan, but the operator changes the reconstruction thickness to 0.5 mm, then the background color of the window of the image pitch. After the alert, the host controller 110 judges whether the value of the image pitch is changed by the operator or not (Step 45). Subsequently, in a certain period of time, if such value is changed, the host controller 110 judges the value is appropriate or not with reference to a table, for example (Step 46).

If the value is appropriate, it stands by to next processing timing, and processing is returned to Step 43 (Steps 47 and 48). On the other hand, if it is judged that the value of the image pitch is not changed in Step 45, it stands by further, repeating the judgment for a certain period of time (Step 49). If the value of the image pitch is not changed for the certain period of time, scanning prohibition processing for forbidding the helical scan is performed (for example, a prohibition flag is stood) and the prohibition information is displayed on the imaging planning creation screen.

Since the operator is urged to change the image pitch according to the changed reconstruction thickness in the middle of making the imaging plan, the imaging conditions can be set certainly and it is enabled to suppress the degradation of quality-of-image or the increase of the X-ray doze as same as the second example.

The present invention is not limited to the above embodiment, and various modifications may be made without departing from the spirit or scope of the general inventive concept. For example, in the above-mentioned embodiment, although ROTATE/ROTATE type where an X-ray tube and a detector rotate around the patient is explained, (STATIONARY/ROTATE) type where the array of many detection elements are arranged as the shape of a ring and the only an X-ray tube rotates around the patient may be used. Moreover, although the case where the about 360 degrees projection data around the patient is used for the reconstruction is explained in the above embodiment, any reconstruction algorithm like a half scan where 180 degree and view angle projection data may be used. Furthermore, although the above-mentioned embodiment explains the indirect conversion type detector where the X-ray changes into the light with the scintillator and the light is converted to into an electric charge with light-electronic conversion elements, such as a photo-diode, the direct type detector where the X-ray directly changes to an electric charge with the semiconductor material where the electron hole pair is generated and moves each side may be used. Moreover, in the above-mentioned embodiment, although one X-ray tube type X-ray CT apparatus is explained, two or more pairs of an X-ray tube and an X-ray detector, so-called multi X-ray tube type X-ray CT apparatus may be used.

What is claimed is:

1. A computed tomography apparatus, comprising:
   a radiation source configured to emit a radiation through an object;
   a detector configured to detect the radiation passed through the object and output a corresponding output signal;
   a data collection unit configured to collect projection data based on the output signal of the detector; and
   a controller configured to control a display so as to display at least one of a plurality of reconstruction methods and corresponding reconstruction method grade information defining a qualitative factor characteristic of imaging performed by the respective at least one of a plurality of reconstruction methods on said display.

2. The computed tomography apparatus according to claim 1, wherein the grade information comprises a qualitative factor related to at least one of:
   a radiation dose;
   a scanning time;
   a total time from scan to reconstruction;
   a quality of image; and
   an over load protection of the radiation source.

3. The computed tomography apparatus according to claim 1, wherein each of the displayed reconstruction methods comprises:
   a name; and
   a reconstruction method parameter.

4. The computed tomography apparatus according to claim 1, further comprising:
   an image slice width input device configured to input an image slice width of the object,
   wherein the controller is additionally configured to automatically select at least one candidate reconstruction method from a plurality of candidate reconstruction methods according to criteria corresponding to the inputted image slice width and display the selected reconstruction method on the display.

5. The computed tomography apparatus according to claim 1, wherein the plurality of candidate reconstruction methods include comprise:
   a fan-beam reconstruction method where the image is reconstructed on the assumption the radiation is perpendicular to a body axis of the object; and
   a cone-beam reconstruction method where the image is reconstructed on basis of the angle of the radiation.

6. The computed tomography apparatus according to claim 1, wherein the detector comprises:
   a plurality of detection elements arranged in two perpendicular directions and configured to output detection element signals.

7. The computed tomography apparatus according to claim 6, further comprising:
   a signal additional unit configured to add the detection elements signals or add the projection data collected by the data collection unit along an object axis.

8. The computed tomography apparatus according to claim 1, further comprising:
   a main data processing unit configured to perform a helical compensation to the projection data before an image is reconstructed.

9. A computed tomography apparatus, comprising:
   a radiation source configured to emit a radiation through an object;
   a detector configured to detect the radiation passed through the object and output a corresponding output signal;
   a data collection unit configured to collect projection data based on the output signal of the detector;
   an input device configured to input an image slice width of the object;
   a controller configured to perform a priority processing in which a reconstruction method is set according to an order of priority of at least one predetermined feature of the reconstruction method so as to produce a processing result; and
   a reconstruction unit configured to reconstruct an image of the object on the basis of the projection data with a selected reconstruction method selected according to the image slice width and the processing result.

10. The computed tomography apparatus according to claim 9, wherein the at least one predetermined feature of each reconstruction method comprises at least one of:
   a radiation dose;
   a scanning time;
   a total time from scan to reconstruction;
   a quality of image; and
   an over load protection of the radiation source.

11. The computed tomography apparatus according to claim 9, wherein the detector comprises:
   a plurality of detection elements arranged in two perpendicular directions and configured to output detection element signal.

12. The computed tomography apparatus according to claim 11, further comprising:
   a signal additional unit configured to add the detection elements signals or add the projection data collected by the data collection unit along an object axis.

13. The computed tomography apparatus according to claim 9, further comprising:
   a main data processing unit configured to perform a helical compensation to the projection data before an image is reconstructed.

14. A computed tomography apparatus, comprising:
   a radiation source configured to emit a radiation through an object;
   a detector including a plurality of detection elements configured to detect the radiation passed through the object and output an output signal;
   a data collection unit configured to collect projection data based on the output signal of the detector;
   a movement mechanism configured to move the detector toward the object helically with a helical pitch;
   an input device configured to change a number of image slices of the object; and
   a controller configured to give an alarm configured to alert an operator to confirm the helical pitch when the number of image slices is changed.

15. A computed tomography apparatus, comprising:
   a radiation source configured to emit a radiation through an object;
   a detector including a plurality of detection elements configured to detect the radiation passed through the object and output an output signal;
   a data collection unit configured to collect projection data based on the output signal of the detector;
   an input device configured to change a reconstruction thickness of an image of the object; and
   a controller configured to give an alarm configured to alert an operator to confirm an image pitch when the reconstruction thickness is changed.

* * * * *

UNITED STATES PATENT AND TRADEMARK OFFICE
CERTIFICATE OF CORRECTION

| | | |
|---|---|---|
| PATENT NO. | : 7,103,134 B2 | Page 1 of 1 |
| APPLICATION NO. | : 10/330049 | |
| DATED | : September 5, 2006 | |
| INVENTOR(S) | : Suzuki | |

It is certified that error appears in the above-identified patent and that said Letters Patent is hereby corrected as shown below:

On the title page, Item (30), the Foreign Application Priority Data has been omitted. Item (30) should read:

-- (30)      Foreign Application Priority Data

Dec. 28, 2001      (JP) ..................... 2001-399359
     Dec. 5, 2002      (JP) ..................... 2002-353873 --

Signed and Sealed this

Twenty-eighth Day of November, 2006

JON W. DUDAS
*Director of the United States Patent and Trademark Office*